US012662505B2

(12) United States Patent
Gaspard et al.

(10) Patent No.: US 12,662,505 B2
(45) **Date of Patent: *Jun. 23, 2026**

(54) STEVIOL GLYCOSIDE SOLUBILITY ENHANCERS

(71) Applicant: CARGILL, INCORPORATED, Wayzata, MN (US)

(72) Inventors: Dan S. Gaspard, Victoria, MN (US); Adam T. Zarth, St. Louis Park, MN (US)

(73) Assignee: CARGILL, INCORPORATED, Wayzata, MN (US)

( * ) Notice: Subject to any disclaimer, the term of this patent is extended or adjusted under 35 U.S.C. 154(b) by 1121 days.

This patent is subject to a terminal disclaimer.

(21) Appl. No.: 17/594,136

(22) PCT Filed: Apr. 3, 2020

(86) PCT No.: PCT/US2020/026568

§ 371 (c)(1),
(2) Date: Oct. 4, 2021

(87) PCT Pub. No.: WO2020/210122

PCT Pub. Date: Oct. 15, 2020

(65) Prior Publication Data

US 2022/0162250 A1 May 26, 2022

Related U.S. Application Data

(60) Provisional application No. 62/832,062, filed on Apr. 10, 2019, provisional application No. 62/830,450, filed on Apr. 6, 2019.

(51) Int. Cl.

| | |
|---|---|
| ***C07H 15/256*** | (2006.01) |
| ***A23L 2/60*** | (2006.01) |
| ***A23L 27/30*** | (2016.01) |

(52) U.S. Cl.

CPC .............. *C07H 15/256* (2013.01); *A23L 2/60* (2013.01); *A23L 27/36* (2016.08)

(58) Field of Classification Search

CPC .................................. A23L 27/36; A23L 2/60
See application file for complete search history.

(56) References Cited

U.S. PATENT DOCUMENTS

| | | | |
|---|---|---|---|
| 3,916,028 | A | 10/1975 | Lee |
| 3,924,017 | A | 12/1975 | Lee |
| 4,082,858 | A | 4/1978 | Morita |
| 4,312,856 | A | 1/1982 | Korduner |
| 4,495,170 | A | 1/1985 | Beyts |
| 4,710,583 | A | 12/1987 | Chmurny |
| 4,853,237 | A | 8/1989 | Prinkkila |
| 4,906,480 | A | 3/1990 | Kashket |
| 5,336,513 | A | 8/1994 | Riemer |
| 5,681,569 | A | 10/1997 | Kuznicki |
| 5,788,971 | A | 8/1998 | Togasaki |
| 5,888,549 | A | 3/1999 | Buchholz |
| 6,022,576 | A | 2/2000 | Cirigliano |
| 6,337,095 | B1 | 1/2002 | Jain |
| 6,426,112 | B1 | 7/2002 | Boatright |
| 6,475,544 | B1 | 11/2002 | Hiramoto |
| 6,589,588 | B1 | 7/2003 | Wester |
| 6,635,774 | B2 | 10/2003 | Roden |
| 6,900,240 | B2 | 5/2005 | Empie |
| 6,989,171 | B2 | 1/2006 | Portman |
| 7,279,184 | B2 | 10/2007 | Gow |
| 7,291,352 | B2 | 11/2007 | Gow |
| 7,294,353 | B2 | 11/2007 | Gow |
| 7,651,717 | B2 | 1/2010 | Shioya |
| 7,727,565 | B2 | 6/2010 | Jani |
| 7,750,053 | B2 | 7/2010 | Suzuki |
| 7,767,238 | B2 | 8/2010 | Roy |
| 7,838,044 | B2 | 11/2010 | Abelyan |
| 7,879,376 | B2 | 2/2011 | Boghani |
| 7,939,563 | B2 | 5/2011 | Suzuki |
| 8,017,168 | B2 | 9/2011 | Prakash |
| 8,076,491 | B2 | 12/2011 | Karanewsky |

(Continued)

FOREIGN PATENT DOCUMENTS

| | | |
|---|---|---|
| CN | 1085073 A | 4/1994 |
| CN | 1100894 A | 4/1995 |

(Continued)

OTHER PUBLICATIONS

Balsan G., et al. (2019) Effect of yerba mate and green tea on paraoxonase and leptin levels in patients affected by overweight or obesity and dyslipidemia: a randomized clinical trial. Nutr. J. 18, 5 [10pp]. DOI:10.1186/s12937-018-0426-y.
Bariana D. S., et al. (1965) Chlorogenic acid: further evidence for its antigenic and allergenic activity. Nature 207, 1155-1157. DOI:10.1038/2071155a0.
Enokuchi Y., et al. (2020) Effects of chlorogenic acids on menopausal symptoms in healthy women: a randomized, placebo-controlled, double-blind, parallel-group trial. Nutrients 12, 3757 [12pp]. DOI:10.3390/nu12123757.
Freedman S. O., et al. (1961) Chlorogenic acid: an allergen in green coffee bean. Nature 192, 241-243. DOI:10.1038/192241a0.

(Continued)

*Primary Examiner* — Jeffrey P Mornhinweg

(57) ABSTRACT

A steviol glycoside solubility enhancer may include a mono-caffeoylquinic (MCQ) component that includes at least one compound selected from the group consisting of chlorogenic acid, neochlorogenic acid, cryptochlorogenic acid, and salts thereof; and a dicaffeoylquinic (DCQ) component that includes at least one compound selected from the group consisting of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof. In one suitable implementation, the MCQ component and the DCQ component together comprise more than 50% (wt), preferably more than 60% (wt), more than 70% (wt), more than 80% (wt), more than 90% (wt), or more than 95% (wt) of the steviol glycoside solubility enhancer.

23 Claims, No Drawings

(56) References Cited

U.S. PATENT DOCUMENTS

| | | | |
|---|---|---|---|
| 8,088,428 | B2 | 1/2012 | Yamane |
| 8,092,795 | B2 | 1/2012 | Tsuchiya |
| 8,178,148 | B2 | 5/2012 | Fujii |
| 8,197,875 | B2 | 6/2012 | Chien |
| 8,241,680 | B2 | 8/2012 | Williams |
| 8,337,929 | B2 | 12/2012 | Ogura |
| 8,367,137 | B2 | 2/2013 | Prakash |
| 8,512,789 | B2 | 8/2013 | Prakash |
| 8,524,304 | B2 | 9/2013 | Prakash |
| 8,530,527 | B2 | 9/2013 | Markosyan |
| 8,703,228 | B2 | 4/2014 | Boghani |
| 8,940,350 | B2 | 1/2015 | Prakash |
| 8,940,351 | B2 | 1/2015 | Prakash |
| 8,956,678 | B2 | 2/2015 | Prakash |
| 9,011,956 | B2 | 4/2015 | Prakash |
| 9,060,537 | B2 | 6/2015 | Mutilangi |
| 9,101,160 | B2 | 8/2015 | Prakash |
| 9,101,161 | B2 | 8/2015 | Prakash |
| 9,131,719 | B2 | 9/2015 | Backes |
| 9,133,229 | B2 | 9/2015 | Lee |
| 9,144,251 | B2 | 9/2015 | Prakash |
| 9,149,051 | B2 | 10/2015 | Prakash |
| 9,358,264 | B2 | 6/2016 | Ibarra |
| 9,457,009 | B2 | 10/2016 | Guthrie |
| 9,492,379 | B2 | 11/2016 | Park |
| 9,510,611 | B2 | 12/2016 | Purkayastha |
| 9,629,795 | B2 | 4/2017 | Krammer |
| 9,636,373 | B1 | 5/2017 | Akao |
| 9,775,822 | B2 | 10/2017 | Prasad |
| 9,844,576 | B2 | 12/2017 | Brownell |
| 9,848,624 | B2 | 12/2017 | Ley |
| 9,889,107 | B2 | 2/2018 | Guthrie |
| 9,962,356 | B2 | 5/2018 | Prasad |
| 10,188,125 | B2 | 1/2019 | Ozato |
| 10,376,521 | B2 | 8/2019 | Zaworotko |
| 10,420,744 | B2 | 9/2019 | Prasad |
| 10,602,758 | B2 | 3/2020 | Dubois |
| 10,624,372 | B2 | 4/2020 | Reichelt |
| 10,772,340 | B2 | 9/2020 | Hotta |
| 10,780,170 | B2 | 9/2020 | Purkayastha |
| 10,798,961 | B2 | 10/2020 | Marcq |
| 10,849,339 | B2 | 12/2020 | Prakash |
| 10,874,130 | B2 | 12/2020 | Kim |
| 10,952,458 | B2 | 3/2021 | Purkayastha |
| 10,973,794 | B2 | 4/2021 | Forbes |
| 11,000,497 | B2 | 5/2021 | Prasad |
| 12,097,231 | B2 | 9/2024 | Gaspard et al. |
| 2001/0051195 | A1 | 12/2001 | Miljkovic |
| 2002/0068123 | A1 | 6/2002 | Verhagen |
| 2002/0187239 | A1 | 12/2002 | Miljkovic |
| 2002/0197386 | A1 | 12/2002 | Hiramoto |
| 2003/0003212 | A1 | 1/2003 | Chien |
| 2003/0008943 | A1 | 1/2003 | Slone |
| 2003/0045473 | A1 | 3/2003 | Sarama |
| 2003/0138537 | A1 | 7/2003 | Bailey |
| 2003/0172392 | A1 | 9/2003 | Mendu |
| 2004/0086619 | A1 | 5/2004 | Zhong |
| 2004/0213881 | A1 | 10/2004 | Chien |
| 2005/0079232 | A1 | 4/2005 | Offord-Cavin |
| 2005/0106215 | A1 | 5/2005 | Offord-Cavin |
| 2005/0118293 | A1 | 6/2005 | Gow |
| 2005/0220868 | A1 | 10/2005 | Lahl |
| 2006/0083838 | A1 | 4/2006 | Jackson |
| 2006/0263475 | A1 | 11/2006 | Jani |
| 2006/0280835 | A1 | 12/2006 | Jani |
| 2006/0286202 | A1 | 12/2006 | Boghani |
| 2007/0029258 | A1 | 2/2007 | Takeda |
| 2007/0054023 | A1 | 3/2007 | Bingley |
| 2007/0082106 | A1 | 4/2007 | Lee |
| 2007/0116800 | A1 | 5/2007 | Prakash |
| 2007/0116823 | A1 | 5/2007 | Prakash |
| 2007/0116828 | A1 | 5/2007 | Prakash |
| 2007/0116829 | A1 | 5/2007 | Prakash |
| 2007/0116838 | A1 | 5/2007 | Prakash |
| 2007/0116839 | A1 | 5/2007 | Prakash |
| 2007/0128311 | A1 | 6/2007 | Prakash |
| 2007/0292582 | A1 | 12/2007 | Prakash |
| 2008/0014331 | A1 | 1/2008 | Badalov |
| 2008/0063748 | A1 | 3/2008 | Massey |
| 2008/0107787 | A1 | 5/2008 | Prakash |
| 2008/0226788 | A1 | 9/2008 | Chang |
| 2008/0226790 | A1 | 9/2008 | Johnson |
| 2008/0261916 | A1 | 10/2008 | Jaszberenyi |
| 2008/0286421 | A1 | 11/2008 | DeLease |
| 2008/0292764 | A1 | 11/2008 | Prakash |
| 2008/0292765 | A1 | 11/2008 | Prakash |
| 2008/0292775 | A1 | 11/2008 | Prakash |
| 2009/0004360 | A1 | 1/2009 | Bingley |
| 2009/0053378 | A1 | 2/2009 | Prakash |
| 2010/0028325 | A1 | 2/2010 | Rocabayera Bonvila |
| 2010/0099857 | A1 | 4/2010 | Evans |
| 2010/0112136 | A1 | 5/2010 | Ward |
| 2010/0160224 | A1 | 6/2010 | Thomas |
| 2010/0297327 | A1 | 11/2010 | Stangle |
| 2010/0330244 | A1 | 12/2010 | Nonaka |
| 2011/0033525 | A1 | 2/2011 | Liu |
| 2011/0054022 | A1 | 3/2011 | Poessel |
| 2011/0091394 | A1 | 4/2011 | Abelyan |
| 2011/0104353 | A1 | 5/2011 | Lee |
| 2011/0160311 | A1 | 6/2011 | Prakash |
| 2011/0189360 | A1 | 8/2011 | Yoo |
| 2011/0195161 | A1 | 8/2011 | Upreti |
| 2011/0195170 | A1 | 8/2011 | Shigemura |
| 2011/0293538 | A1 | 12/2011 | Ley |
| 2012/0041078 | A1 | 2/2012 | Tachdjian |
| 2012/0058236 | A1 | 3/2012 | Fosdick |
| 2012/0064221 | A1 | 3/2012 | Given |
| 2012/0076899 | A1 | 3/2012 | Evans |
| 2012/0156351 | A1 | 6/2012 | Miyazawa |
| 2012/0177602 | A1 | 7/2012 | New |
| 2012/0196019 | A1 | 8/2012 | Shi |
| 2012/0201935 | A1 | 8/2012 | Krohn |
| 2013/0039932 | A1 | 2/2013 | Park |
| 2013/0040036 | A1 | 2/2013 | Zeller |
| 2013/0071521 | A1 | 3/2013 | Lee |
| 2013/0209658 | A1 | 8/2013 | Spelman |
| 2013/0251881 | A1 | 9/2013 | Mutilangi |
| 2013/0274351 | A1 | 10/2013 | Markosyan |
| 2013/0316066 | A1 | 11/2013 | Brown |
| 2014/0004215 | A1 | 1/2014 | Brownell |
| 2014/0094453 | A1 | 4/2014 | Tachdjian |
| 2014/0155359 | A1 | 6/2014 | Broze |
| 2014/0171519 | A1 | 6/2014 | Prakash |
| 2014/0206634 | A1 | 7/2014 | Liu |
| 2014/0295049 | A1 | 10/2014 | Ragot |
| 2014/0302180 | A1 | 10/2014 | Chapal |
| 2014/0309294 | A1 | 10/2014 | Erfurt |
| 2014/0342078 | A1 | 11/2014 | Hayes |
| 2015/0017284 | A1 | 1/2015 | Prakash |
| 2015/0050410 | A1 | 2/2015 | Luo |
| 2015/0125587 | A1 | 5/2015 | Asano |
| 2015/0189904 | A1 | 7/2015 | Prakash |
| 2015/0223510 | A1 | 8/2015 | Lee |
| 2015/0289548 | A1 | 10/2015 | Given |
| 2015/0320101 | A1 | 11/2015 | Walton |
| 2015/0328179 | A1 | 11/2015 | Nakashima |
| 2015/0344456 | A1 | 12/2015 | Dull |
| 2015/0366253 | A1 | 12/2015 | Shi |
| 2016/0100689 | A1 | 4/2016 | Wang |
| 2016/0113316 | A1 | 4/2016 | Nachbagauer |
| 2016/0165941 | A1 | 6/2016 | Hofmekler |
| 2016/0183574 | A1 | 6/2016 | Chen |
| 2016/0213039 | A1 | 7/2016 | Kumar |
| 2016/0242452 | A1 | 8/2016 | Mutilangi |
| 2016/0309761 | A1 | 10/2016 | Brower, III |
| 2016/0316797 | A1 | 11/2016 | Piorkowski |
| 2017/0006901 | A1 | 1/2017 | Carlson |
| 2017/0055548 | A1 | 3/2017 | Chakraborty |
| 2017/0095443 | A1 | 4/2017 | Luo |
| 2017/0105432 | A1 | 4/2017 | Karanewsky |
| 2017/0119032 | A1 | 5/2017 | Patron |
| 2017/0119033 | A1 | 5/2017 | Liu |
| 2017/0143012 | A1 | 5/2017 | San Miguel |
| 2017/0156374 | A1 | 6/2017 | Ackilli |

(56) References Cited

U.S. PATENT DOCUMENTS

| | | | |
|---|---|---|---|
| 2017/0172191 | A1 | 6/2017 | Prakash |
| 2017/0183326 | A1 | 6/2017 | Kimoto |
| 2017/0273338 | A1 | 9/2017 | Lee |
| 2017/0295827 | A1 | 10/2017 | Prakash |
| 2017/0303574 | A1 | 10/2017 | Luo |
| 2017/0327776 | A1 | 11/2017 | Chien et al. |
| 2017/0354175 | A1 | 12/2017 | Karanewsky |
| 2017/0362268 | A1 | 12/2017 | Carlson |
| 2018/0000133 | A1 | 1/2018 | Izumi |
| 2018/0002306 | A1 | 1/2018 | Jiang |
| 2018/0086751 | A1 | 3/2018 | Karanewsky |
| 2018/0092381 | A1 | 4/2018 | Brijwani |
| 2018/0103670 | A1 | 4/2018 | Recenti |
| 2018/0168212 | A1 | 6/2018 | Markosyan |
| 2018/0177216 | A1 | 6/2018 | Markosyan |
| 2018/0263269 | A1 | 9/2018 | Prakash |
| 2018/0289042 | A1 | 10/2018 | Bell |
| 2018/0296678 | A1 | 10/2018 | Prakash |
| 2019/0116835 | A1 | 4/2019 | Prakash |
| 2019/0142043 | A1 | 5/2019 | Prakash |
| 2019/0175499 | A1 | 6/2019 | Zhang |
| 2019/0274985 | A1 | 9/2019 | Hotta |
| 2019/0313669 | A1 | 10/2019 | Dubois |
| 2020/0009208 | A1 | 1/2020 | Hwang |
| 2020/0023021 | A1 | 1/2020 | Lewis |
| 2020/0054058 | A1 | 2/2020 | Prakash |
| 2020/0085778 | A1 | 3/2020 | Yamamoto |
| 2020/0138056 | A1 | 5/2020 | Graz |
| 2020/0138765 | A1 | 5/2020 | Prasad |
| 2020/0154737 | A1 | 5/2020 | Dubois |
| 2020/0196649 | A1 | 6/2020 | Mitchell |
| 2020/0197342 | A1 | 6/2020 | Russo |
| 2020/0237845 | A1 | 7/2020 | Suzuki |
| 2020/0275682 | A1 | 9/2020 | Chakraborty |
| 2020/0305483 | A1 | 10/2020 | Gan |
| 2020/0345049 | A1 | 11/2020 | Galano |
| 2021/0037851 | A1 | 2/2021 | Fraser |
| 2021/0051976 | A1 | 2/2021 | Fraser |
| 2021/0084949 | A1 | 3/2021 | Banavara |
| 2021/0092986 | A1 | 4/2021 | Dubois |
| 2021/0128600 | A1 | 5/2021 | Rauch |
| 2021/0153536 | A1 | 5/2021 | Ozato |
| 2021/0236450 | A1 | 8/2021 | Guthrie |
| 2021/0260013 | A1 | 8/2021 | Lee |
| 2021/0267243 | A1 | 9/2021 | Peterson |
| 2024/0050506 | A1 | 2/2024 | Gaspard et al. |

FOREIGN PATENT DOCUMENTS

| | | | |
|---|---|---|---|
| CN | 1144459 | A | 3/1997 |
| CN | 1336333 | A | 2/2002 |
| CN | 1615838 | A | 5/2005 |
| CN | 1651398 | A | 8/2005 |
| CN | 1253099 | | 4/2006 |
| CN | 100341500 | C | 10/2007 |
| CN | 102381974 | A | 3/2012 |
| CN | 102771751 | A | 11/2012 |
| CN | 102860438 | A | 1/2013 |
| CN | 104397785 | A | 3/2015 |
| CN | 102924544 | B | 4/2015 |
| CN | 103656627 | B | 9/2015 |
| CN | 103874411 | A | 6/2016 |
| CN | 106138298 | A | 11/2016 |
| CN | 107184482 | A | 9/2017 |
| CN | 107455718 | A | 12/2017 |
| DE | 29603759 | U1 | 5/1996 |
| DE | 29808384 | U1 | 8/1998 |
| EP | 0730830 | B1 | 9/1996 |
| EP | 1186297 | A2 | 3/2002 |
| EP | 1903890 | A | 4/2008 |
| EP | 1716757 | B1 | 7/2009 |
| EP | 1925208 | B1 | 12/2011 |
| EP | 2340719 | B1 | 2/2014 |
| EP | 2896301 | B1 | 6/2016 |
| EP | 2643007 | B1 | 8/2016 |
| EP | 3052074 | | 8/2016 |
| EP | 2625962 | B1 | 6/2017 |
| EP | 3188604 | A1 | 7/2017 |
| EP | 3257507 | A1 | 12/2017 |
| EP | 3264919 | A1 | 1/2018 |
| EP | 3097790 | B1 | 5/2018 |
| EP | 2409696 | B1 | 6/2018 |
| EP | 2753188 | B1 | 1/2019 |
| EP | 2856883 | B1 | 3/2019 |
| EP | 2692243 | B1 | 6/2019 |
| EP | 3397072 | B1 | 7/2019 |
| EP | 3513663 | A1 | 7/2019 |
| EP | 3169166 | B1 | 8/2019 |
| EP | 3524062 | A2 | 8/2019 |
| EP | 2934181 | B1 | 9/2019 |
| EP | 2124647 | B2 | 12/2019 |
| EP | 3228195 | B1 | 1/2020 |
| EP | 3544445 | B1 | 5/2020 |
| FR | 2138067 | B1 | 6/1976 |
| GB | 2348104 | A | 5/1999 |
| JP | 54147976 | A | 11/1979 |
| JP | 63173531 | A | 7/1988 |
| JP | 0195739 | A | 4/1989 |
| JP | 0427374 | A | 1/1992 |
| JP | 04145048 | A | 5/1992 |
| JP | 0638723 | A | 2/1994 |
| JP | 07123921 | A | 5/1995 |
| JP | 07135938 | A | 5/1995 |
| JP | 0823939 | A | 1/1996 |
| JP | 0994080 | A | 4/1997 |
| JP | 09221667 | A | 8/1997 |
| JP | 09266767 | A | 10/1997 |
| JP | 10179079 | A | 7/1998 |
| JP | 10183164 | A | 7/1998 |
| JP | 10248501 | A | 9/1998 |
| JP | 119189 | A | 1/1999 |
| JP | 11299473 | A | 11/1999 |
| JP | 2000063827 | A | 2/2000 |
| JP | 2000308477 | A | 11/2000 |
| JP | 2001321115 | A | 11/2001 |
| JP | 2003204756 | A | 7/2003 |
| JP | 2002021938 | A1 | 1/2004 |
| JP | 2004528050 | A | 9/2004 |
| JP | 2006006318 | A | 1/2006 |
| JP | 2006104229 | A | 4/2006 |
| JP | 2007143528 | A | 6/2007 |
| JP | 2008-094759 | A | 4/2008 |
| JP | 2009517022 | A | 4/2009 |
| JP | 2009523407 | A | 6/2009 |
| JP | 2010521166 | A | 6/2010 |
| JP | 2011045305 | A | 3/2011 |
| JP | 2011168543 | A | 9/2011 |
| JP | 2012005483 | A | 1/2012 |
| JP | 2012110322 | A | 6/2012 |
| JP | 2012240949 | A | 12/2012 |
| JP | 2011071179 | A | 4/2013 |
| JP | 2015506718 | A | 3/2015 |
| JP | 2015511498 | A | 4/2015 |
| JP | 2017121221 | A | 7/2017 |
| JP | 2017123788 | A | 7/2017 |
| JP | 2016084887 | A | 9/2017 |
| JP | 2018085964 | A | 6/2018 |
| JP | 6710115 | B2 | 6/2020 |
| JP | 2019230013 | A | 6/2020 |
| JP | 2020-536537 | A | 12/2020 |
| JP | 2021-099038 | A | 7/2021 |
| KR | 101500485 | B1 | 3/2015 |
| PH | 12011000255 | A | 7/2011 |
| WO | 1998042209 | A1 | 10/1998 |
| WO | 1999030576 | W | 6/1999 |
| WO | 2000030464 | A1 | 6/2000 |
| WO | 2000062628 | A1 | 10/2000 |
| WO | 2000069282 | A1 | 11/2000 |
| WO | 2001097624 | A1 | 12/2001 |
| WO | 02/21938 | A1 | 3/2002 |
| WO | 2002041700 | A1 | 5/2002 |
| WO | 02100192 | W | 12/2002 |
| WO | 2002096852 | A1 | 12/2002 |
| WO | 2007013616 | A1 | 2/2007 |

(56) References Cited

FOREIGN PATENT DOCUMENTS

| | | | |
|---|---|---|---|
| WO | 2007/061900 | A1 | 5/2007 |
| WO | 2007061753 | A2 | 5/2007 |
| WO | 2007061795 | A1 | 5/2007 |
| WO | 2007149672 | A2 | 12/2007 |
| WO | 2008057965 | A2 | 5/2008 |
| WO | 2008093892 | A1 | 8/2008 |
| WO | 2008147723 | A1 | 12/2008 |
| WO | 2008147725 | A1 | 12/2008 |
| WO | 2009012051 | A1 | 1/2009 |
| WO | 2010038911 | A1 | 4/2010 |
| WO | 2011/071179 | A1 | 6/2011 |
| WO | 11094423 | W | 8/2011 |
| WO | 2011094423 | A1 | 8/2011 |
| WO | 2011105561 | A1 | 9/2011 |
| WO | 2011106114 | A1 | 9/2011 |
| WO | 2011112892 | A1 | 9/2011 |
| WO | 2012083251 | A1 | 6/2012 |
| WO | 2012107205 | A1 | 8/2012 |
| WO | 2012109506 | A1 | 8/2012 |
| WO | 2012166164 | A1 | 12/2012 |
| WO | 2013096420 | A1 | 6/2013 |
| WO | 2013148177 | A1 | 10/2013 |
| WO | 2014104408 | A1 | 7/2014 |
| WO | 2014146135 | A2 | 9/2014 |
| WO | 2014153000 | A1 | 9/2014 |
| WO | 2015023928 | A1 | 2/2015 |
| WO | 2015024218 | A1 | 2/2015 |
| WO | 2015117011 | A1 | 8/2015 |
| WO | 2016036578 | A1 | 3/2016 |
| WO | 2016049236 | A1 | 3/2016 |
| WO | 2016073251 | A1 | 5/2016 |
| WO | 2016/084887 | A1 | 6/2016 |
| WO | 16085919 | W | 6/2016 |
| WO | 16085924 | W | 6/2016 |
| WO | 16086233 | W | 6/2016 |
| WO | 2016100689 | A1 | 6/2016 |
| WO | 17053980 | W | 3/2017 |
| WO | 2017059414 | A1 | 4/2017 |
| WO | 2017095932 | A1 | 6/2017 |
| WO | 17120480 | W | 7/2017 |
| WO | 17189994 | W | 11/2017 |
| WO | 2017196933 | A1 | 11/2017 |
| WO | 2018013739 | A2 | 1/2018 |
| WO | 2018102447 | A2 | 6/2018 |
| WO | 2019071182 | A1 | 4/2019 |
| WO | 2019071187 | A1 | 4/2019 |
| WO | 2019071188 | A1 | 4/2019 |
| WO | 2019071220 | A1 | 4/2019 |
| WO | 2019071250 | A1 | 4/2019 |
| WO | 2019071254 | A1 | 4/2019 |
| WO | 19177634 | W | 9/2019 |
| WO | 2019177634 | A1 | 9/2019 |
| WO | 19222601 | W | 11/2019 |
| WO | 2020172276 | W | 8/2020 |
| WO | 2020202193 | W | 10/2020 |
| WO | 2020210118 | A1 | 10/2020 |
| WO | 2020210122 | A1 | 10/2020 |
| WO | 2020210160 | A2 | 10/2020 |
| WO | 2020237060 | A1 | 11/2020 |
| WO | 2021038830 | A1 | 3/2021 |
| WO | 2021038832 | A1 | 3/2021 |
| WO | 2021049864 | A1 | 3/2021 |
| WO | 2021081417 | A1 | 4/2021 |
| WO | 2021090989 | A1 | 5/2021 |
| WO | 2021091322 | A1 | 5/2021 |
| WO | 2021091327 | A1 | 5/2021 |
| WO | 2021125070 | A1 | 6/2021 |
| WO | 2021132439 | A1 | 7/2021 |

OTHER PUBLICATIONS

Freedman S. O., et al. (1964) Antigenic and allergenic properties of chlorogenic acid man, rabbit, guinea pig. Can. Med. Assoc. J. 90, 473-474.

Gebara K. S., et al. (2020) A randomized crossover intervention study on the effect a standardized maté extract (*Ilex paraguariensis* A. St.-Hil.) in Men predisposed to cardiovascular risk. Nutrients, 13, 14 [14pp]. DOI:10.3390/nu13010014.

Gu R., et al. (2007) Simultaneous determination of 1,5-dicaffeoylquinic acid and its active metabolites in human plasma by liquid chromatography-tandem mass spectrometry for pharmacokinetic studies. J. Chromatogr. B. 852, 85-91. DOI:10.1016/j.jchromb.2006.12.055.

International Search Report and Written Opinion mailed Jul. 28, 2020 of PCT/US2020/026524 (14 pages).

Jin S., et al. (2015) Chlorogenic acid improves late diabetes through adiponectin receptor signaling pathways in db/db mice. PLoS ONE 10, e0120842 [15pp]. DOI:10.1371/journal.pone.0120842.

Kato M., et al. (2018) Effect of chlorogenic acid intake on cognitive function in the elderly: a pilot study. Evid. Based. Complement. Alternat. Med. 2018, Article ID 8608497 [8pp]. DOI:10.1155/2018/8608497.

Laird Layton L., et al. (1964) Pure chlorogenic acid is not allergenic in atopy to green coffee: A specific protein probably is involved. Nature 203, 188-189. DOI:10.1038/203188a0.

Lin M., et al. (2013) Evaluation of the potential sensitization of chlorogenic Acid: a meta-analysis. Evid. Based. Complement. Alternat. Med. 2013, Article ID 208467 DOI:10.1155/2013/208467.

Liu B., et al. (2017) Preparation, phytochemical investigation, and safety evaluation of chlorogenic acid products from Eupatorium adenophorum. Molecules 22, 67 [12pp]. DOI:10.3390/molecules22010067.

Liu Z., et al. (2010) Evaluation of the immunosensitizing potential of chlorogenic acid using a popliteal lymph node assay in BALB/c mice. Food Chem. Toxicol. 48, 1059-1065. DOI:10.1016/j.fct.2010.01.024.

Lowell F. C. (1965) Allergenicity of chlorogenic acid. J. Allergy 36, 308. DOI:10.1016/0021-8707(65)90091-2.

Mikulasova M., et al. (2005) Genotoxic effects of the hydroxycinnamic acid derivatives—caffeic, chlorogenic and cichoric acids. Biologia (Bratisl.) 60, 275-279.

Minuzzi Becker A., et al. (2019) Spray-dried yerba mate extract capsules: clinical evaluation and antioxidant potential in healthy individuals. Plant oods Hum. Nutr. 74, 495-500 [plus supplementary tables]. DOI:10.1007/s11130-019-00764-4.

Monteiro M., et al. (2007) Chlorogenic acid compounds from coffee are differentially absorbed and metabolized in humans. J. Nutr. 137, 2196-2201. DOI:10.1093/jn/137.10.2196.

Nakamura S., et al. (2006) [Pharmacokinetics of chlorogenic acids absorbed in human plasma and their metabolites following oral ingestion of coffee drink]. Yakuri To Chiryo [Jpn. Pharmacol. Ther.] 34, 1239-1246.

Naylor L. H., et al. (2021) Acute dose-response effect of coffee-derived chlorogenic acids on the human vasculature in healthy volunteers: a randomized controlled trial. Am. J. Clin. Nutr. 113, 370-379. DOI:10.1093/ajcn/nqaa312.

Nowacki L. C., et al. (2021) Ilex paraguariensis extract as an alternative to pain medications. Acta Pharm. 71, 383-398. DOI:10.2478/acph-2021-0029.

Ochiai R., et al. (2019) Effect of chlorogenic acids on cognitive function in mild cognitive impairment: a randomized controlled crossover trial. J. Alzheimers Dis. 72, 1209-1216 [plus supplementary tables]. DOI:10.3233/jad-190757.

Olthof M. R., et al. (2001a) Consumption of high doses of chlorogenic acid, present in coffee, or of black tea increases plasma total homocysteine concentrations in humans. Am. J. Clin. Nutr. 73, 532-538. DOI:10.1093/ajcn/73.3.532.

Olthof M. R., et al. (2001b) Chlorogenic acid and caffeic acid are absorbed in humans. J. Nutr. 131, 66-71. DOI:10.1093/jn/131.1.66.

Olthof M. R., et al. (2003) Chlorogenic acid, quercetin-3-rutinoside and black tea phenols are extensively metabolized in humans. J. Nutr. 133, 1806-1814 [erratum, 133, 2692]. DOI:10.1093/jn/133.6.1806.

Onakpoya I. J., et al. (2015) The effect of chlorogenic acid on blood pressure: a systematic review and meta-analysis of randomized clinical trials. J. Hum. Hypertens. 29, 77-81 [plus supplementary data]. DOI:10.1038/jhh.2014.46.

(56) References Cited

OTHER PUBLICATIONS

Park I., et al. (2017) Effects of subacute ingestion of chlorogenic acids on sleep architecture and energy metabolism through activity of the autonomic nervous system: a randomised, placebo-controlled, double-blinded cross-over trial. Br. J. Nutr. 117, 979-984. DOI:10.1017/S0007114517000587.

Pereira Panza V., et al. (2019) Effect of mate tea (*Ilex paraguariensis*) on the expression of the leukocyte NADPH oxidase subunit p47phox and on circulating inflammatory cytokines in healthy men: a pilot study. Int. J. Food Sci. Nutr. 70, 212-221DOI:10.1080/09637486.2018.1486393.

Phenolaeis.com Accessed Aug. 24, 2022 Palm Fruit Extract compositions and applications.

Plumb G. W., et al. (1999) Metabolism of chlorogenic acid by human plasma, liver, intestine and gut microflora. J. Sci. Food Agric. 79, 390-392. DOI:10.1002/(SICI)1097-0010(19990301)79:3<390::AID-JSFA258>3.0.CO;2-0.

Prakash et al., "Catalytic Hydrogenation of the Sweet Principles of Stevia rebaudiana, Rebaudioside B, Rebaudioside C, and Rebaudioside D and Sensory Evaluation of Their Reduced Derivatives", Int. J. Mol. Sci. 2012, 13, 15126-15136; doi:10.3390/ijms131115126.

Renouf M., et al. (2014) Dose-response plasma appearance of coffee chlorogenic and phenolic acids in adults. Mol. Nutr. Food Res. 58, 301-309. DOI:10.1002/mnfr.201300349.

Richling E., et al. (2012) Dose-response relationship of chlorogenic acids in humans. Naunyn Schmiedebergs ArchPharmacol. 385, S75 [abstract 327]. DOI:10.1007/s00210-012-0736-0.

Rogerio De Sousa W., et al. (2019) Evaluation of reproductive toxicology of aqueous extract of yerba mate (*Ilex paraguariensis* A. St.-Hil.), a traditional South American beverage. J. Med. Food 22, 97-101. DOI:10.1089/jmf.2018.0060.

Sanchez Boado L., et al (2018) Effects of llex paraguariensis polyphenols on magnesium absorption and iron bioavailability: preliminary study. J. Food Res. 7, 114-126. DOI:10.5539/jfr.v7n2p114.

Sarria B., et al. (2020a) Yerba mate may prevent diabetes according to a crossover, randomized, controlled study in humans. Proc. Nutr. Soc. 79, OCE2, E245 DOI:10.1017/S0029665120001937.

Sarria B., et al. (2020b) Yerba mate improves cardiovascular health in normocholesterolemic and hypercholesterolemic subjects. Proc. Nutr. Soc. 79, OCE2, E635. DOI: 10.1017/S0029665120005844.

Shinomiya K., et al. (2004) Effects of chlorogenic acid and its metabolites on the sleep-wakefulness cycle in rats. Eur. J. Pharmacol. 504, 185-189. DOI:10.1016/j.ejphar.2004.09.054.

Song Z., et al. (2014) [Effect of chlorogenic acid at high dose on expression of hepatic inflammatory cytokines mRNA induced by lipopolysaccharides]. Ying Yang Xue Bao [Acta Nutr. Sin.] 36, 481-485.

Stalmach A., et al. (2009) Metabolite profiling of hydroxycinnamate derivatives in plasma and urine after the ingestion of coffee by humans: identification of biomarkers of coffee consumption. Drug Metab. Dispos. 37, 1749-1758. DOI:10.1124/dmd.109.028019.

Stalmach A., et al. (2010) Bioavailability of chlorogenic acids following acute ingestion of coffee by humans with an ileostomy. Arch. Biochem. Biophys. 501, 98-105. DOI:10.1016/j.abb.2010.03.005.

Stich H. F., et al. (1981) A comparative genotoxicity study of chlorogenic acid (3-O-caffeoylquinic acid). Mutat. Res. 90, 201-212. DOI:10.1016/0165-1218(81)90001-X.

Suzuki A., et al. (2006) Chlorogenic acid attenuates hypertension and improves endothelial function in spontaneously hypertensive rats. J. Hypertens. 24, 1065-1073. DOI:10.1097/01.hjh.0000226196.67052.c0.

U.S. FDA (1993) Appendix I. Table 14. Conversion table for test chemical treatment doses used in PAFA. In Priority Based Assessment of Food Additives (PAFA) Database. U.S. Food and Drug Administration (U.S. FDA), Center for Food Safety & Applied Nutrition (CFSAN), Washington, DC, p. 58.

Wang Y., et al. (2018) [Effects of chlorogenic acid on growth performance, serum immunoglobulins, intestinal mucosa morphology, digestive and absorptive capacity of piglets]. Chin. J. Anim. Nutr. 30, 1136-1145 [DOI:10.7506/spkx1002-6630-201709026.

Watanabe T., et al. (2019) Coffee abundant in chlorogenic acids reduces abdominal fat in overweight adults: a randomized, double-blind, controlled trial. Nutrients 11, 1617 [13pp]. DOI:10.3390/nu11071617.

Wei Z.-M., et al. (2010) [Clinical tolerability of 1,5-dicaffeoylquinic acid tablets]. Zhongguo Xin Yao Za Zhi [Chin. J. New Drugs] 19, 106-108.

Yang B., et al. (2005) Metabolic profile of 1,5-dicaffeoylquinic acid in rats, an in vivo and in vitro study. Drug Metab. Dispos. 33, 930-936. DOI:10.1124/dmd.104.002154.

Zhu Y., et al. (2017) [Effect of caffeine and chlorogenic acid on body weight, lipid accumulation and the expression of lipid metabolism-related genes in high-fat diet-fed mice]. Shipin Kexue [Food Sci.] 38, 162-167 DOI:10.7506/spkx1002-6630-201709026.

Zuniga L. Y., et al. (2018) Effect of chlorogenic acid administration on glycemic control, insulin secretion, and insulin sensitivity in patients with impaired glucose tolerance. J. Med. Food 21, 469-473. DOI:10.1089/jmf.2017.0110.

Abeywardena M. Y., et al. (2010) Acute administration of chlorogenic acid reduces blood pressure in the rat. Hypertension 55, 1493 [abstract 002]. DOI:10.1161/HYP.0b013e3181df4279.

Albas C. S., et al.(2014) Avaliação da genotoxicidade da llex paraguariensis (erva mate) pelo teste do micronúcleo / [Evaluation of the genotoxicity of Ilex paraguariensis (yerba mate) by micronucleus test]. Rev. Bras. Plantas Med. 16, 2, Suppl 1, 345-349 [Portuguese, English abstract]. DOI:10.1590/1983-084X/12_058.

Alkhatib A. and Atcheson, R. (2017) Yerba maté (ilex paraguariensis) metabolic, satiety, and mood state effects at rest and during prolonged exercise. Nutrients 9, 882 [15pp]. DOI:10.3390/nu9080882.

Baeza Gema et al: "Dihydrocaffeic acid, a major microbial metabolite of chlorogenic acids, shows similar protective effect than a yerba mate phenolic extract against oxidative stress in HepG2 cells", Food Research International, Elsevier, Amsterdam, NL, vol. 87, Jun. 17, 2016 (Jun. 17, 2016), pp. 25-33, XP029671195, ISSN: 0963-9969, DOI: 10.1016/J.FOODRES.2016.06.011.

Bidau C. J., et al. (2004) Evaluation of the genotoxicity of aqueous extracts of Ilex paraguariensis St. Hil. (Aquifoliaceae) using the Allium test. Cytologia 69, 109-117. DOI:10.1508/cytologia.69.109.

Boaventura B. C., et al.(2012) Association of mate tea (*Ilex paraguariensis*) intake and dietary intervention and effects on oxidative stress biomarkers of dyslipidemic subjects. Nutrition 28, 657-664. DOI:10.1016/j.nut.2011.10.017.

Boaventura B. C., et al.(2013) Antioxidant potential of mate tea (*Ilex paraguariensis*) in type 2 diabetic mellitus and pre-diabetic individuals. J. Funct. Foods 5, 1057-1064. DOI:10.1016/j.jff.2013.03.001.

Boaventura B. C., et al.(2015) Effect of yerba mate (Ilex paraguariensis A. St. Hil.) infusion obtained by freeze concentration technology on antioxidant status of healthy individuals. LWT Food Sci. Technol. 62, 948-954. DOI:10.1016/j.lwt.2015.02.028.

Boaventura, B. C. B., et al.(2013). Enhancement of bioactive compounds content and antioxidant activity of aqueous extract of mate (Ilex paraguariensis A. St. Hil.) through freeze concentration technology. Food Research International, 53, 686e692.

Borges M. C., et al. (2013) The effect of mate tea (*Ilex paraguariensis*) on metabolic and inflammatory parameters in high-fat diet-fed Wistar rats. Int. J. Food Sci. Nutr. 64, 561-569. DOI:10.3109/09637486.2012.759188.

Bortoluzzi M.-C., et al (2014) Frequency of micronucleus in oral epithelial cells after exposure to mate-tea in healthy humans. Med. Oral Patol. Oral Cir. Bucal. 19, e345-e349. DOI:10.4317/medoral.19570.

Carvalho Ribeiro M., et al (2017) The effects of roasted yerba mate (Ilex paraguariensis A. St. Hil.) consumption on glycemia and total serum creatine phosphokinase in patients with traumatic brain injury. J. Funct. Foods 28, 240-245. DOI:10.1016/j.jff.2016.11.

Chaube S. and Swinyard C. A. (1976) Teratological and toxicological studies of alkaloidal and phenolic compounds from *Solanum tuberosum* L. Toxicol. Appl. Pharmacol. 36, 227-237. DOI:10.1016/0041-008X(76)90002-8.

(56) References Cited

OTHER PUBLICATIONS

Chen J., et al. (2018) Dietary chlorogenic acid improves growth performance of weaned pigs through maintaining antioxidant capacity and intestinal digestion and absorption function. J. Anim. Sci. 96, 1108-1118. DOI:10.1093/jas/skx078.
Cuesta A., et al.(2018) Efecto agudo del consumo de yerba mate (Ilex paraguariensis) sobre el ritmo cardíaco en pacientes derivados para estudio Holter [Acute effect of yerba mate (Ilex paraguariensis) consumption on heart rhythm in patients referred for Holter study] [epub ahead of print]. Arch. Cardiol. Mex. xxx, Jun. 2, 2018 [1-6] [Spanish, English abstract]. DOI:10.1016/j.acmx.2018.05.004.
De Andrade F., Coehlo de Albuquerque C. A., Maraschin M. and da Silva E. L. (2012) Safety assessment of yerba mate (Ilex paraguariensis) dried extract: results of acute and 90 days subchronic toxicity studies in rats and rabbits. Food Chem. Toxicol. 50, 328-334. DOI:10.1016/j.fct.2011.08.028.
De Meneses Fujii et al. (2014) Yerba Mate (Ilex paraguariensis) modulates NF-kappaB pathway and AKT expression in the liver of rats fed on a high-fat diet. Int. J. Food Sci. Nutr. 65, 967-976. DOI:10.3109/09637486.2014.945153.
De Morais E. C., et al (2009) Consumption of yerba mate (Ilex paraguariensis) improves serum lipid parameters in healthy dyslipidemic subjects and provides an additional LDL-cholesterol reduction in individuals on statin therapy. J. Agric. Food Chem. 57, 8316-8324. DOI:10.1021/jf901660g.
Eklund A. (1975) Effect of chlorogenic acid in a casein diet for rats. Nutritional and pathological observations. Nutr. Metab. 18, 258-264. DOI:10.1159/000175603.
Erk T., et al. (2012) Dose-dependent absorption of chlorogenic acids in the small intestine assessed by coffee consumption in ileostomists. Mol. Nutr. Food Res. 56, 1488-1500. DOI:10.1002/mnfr.201200222.
Folwarczna J., et al. (2012) Effects of caffeic and chlorogenic acids on bone mechanical properties in female rats. Bone 50, Suppl. 1, S158 [abstract PP306]. DOI:10.1016/j.bone.2012.02.495.
Fonseca C. A., et al (2000) Nontoxic, mutagenic, and clastogenic activities of mate-chimarrao (Ilex paraguariensis). J. Environ. Pathol. Toxicol. Oncol. 19, 333-346.
Frank J., et al. (2003) The dietary hydroxycinnamate caffeic acid and its conjugate chlorogenic acid increase vitamin E and cholesterol concentrations in Sprague-Dawley rats. J. Agric. Food Chem. 51, 2526-2531. DOI:10.1021/jf026127k.
Gómez-Juaristi M., Martínez-López S., Sarria B., Bravo L. and Mateos R. (2018) Absorption and metabolism of yerba mate phenolic compounds in humans. Food Chem. 240, 1028-1038. DOI:10.1016/j.foodchem.2017.08.003.
Gonthier M.-P., et al. (2006) Microbial metabolism of caffeic acid and its esters chlorogenic and caftaric acids by human faecal microbiota in vitro. Biomed. Pharmacother. 60, 536-540. DOI:10.1016/j.biopha.2006.07.084.
Grzesiuk J. D., et al (2012) Evaluation of mutagenicity and antimutagenicity of Ilex paraguariensi} A. St.-Hil.: Aquifoliaceae infusion on Allium cepa assay. Arq. Cienc. Saude UNIPAR 16, 73-78. DOI:10.25110/arqsaude.v16i2.2012.4840.
Hernandes L. C., et al. (2016) Cytotoxicity and genotoxicity of chlorogenic acid alone or associated with the demethylating drug 5-azacytidine in Jurkat cells. Toxicol. Lett. 258, Suppl. S, S56 [abstract OSC01-007]. DOI:10.1016/j.toxlet.2016.06.1295.
IARC (1991) Mate. In Coffee, Tea, Mate, Methylxanthines and Methylglyoxal. IARC Working Group, Feb. 27-Mar. 6, 1990, Lyon. IARC Monographs on the Evaluation of Carcinogenic Risks to Humans, vol. 51, pp. 273-287. World Health Organization (WHO), International Agency for Research on Cancer (IARC).
IARC (2018) Drinking mate and very hot beverages. In Drinking Coffee, Mate, and Very Hot Beverages. Expert Opinions of IARC Working Group on the Evaluation of Carcinogenic Risks to Humans, May 24-31, 2016, Lyon, France. IARC Monographs on the Evaluation of Carcinogenic Risks to Humans, vol. 116, pp. 427-496. Lyon, France: International Agency for Research on Cancer (IARC), Lyon, France.
Kim H. J., et al. (2012) Effect of green mate in overweight volunteers: a randomised placebo-controlled human study. J. Funct. Foods 4, 287-293. DOI:10.1016/j.jff.2011.12.005.
Kim S.-Y., et al. (2015) Anti-obesity effects of Yerba Mate (Ilex paraguariensis): a randomized, double-blind, placebo-controlled clinical trial. BMC Complement. Altern. Med. 15, 338 [8pp]. DOI:10.1186/s12906-015-0859-1.
Klein G. A., et al (2011) Mate tea (*Ilex paraguariensis*) improves glycemic and lipid profiles of type 2 diabetes and pre-diabetes individuals: a pilot study. J. Am. Coll. Nutr. 30, 320-332.
Kujawska M (2018) Yerba mate (Ilex paraguariensis) beverage: nutraceutical ingredient or conveyor for the intake of medicinal plants? Evidence from Paraguayan folk medicine. Evid. Based. Complement. Alternat. Med. 2018, Article ID 6849317 [17pp]. DOI:10.1155/2018/6849317.
Leitão A. C. and Braga R. S. (1994) Mutagenic and genotoxic effects of mate (Ilex paraguariensis) in prokaryotic organisms. Braz. J. Med. Biol. Res. 27, 1517-1525.
Lorena Deladino et al: "Major Phenolics in Yerba Mate Extracts (Ilex paraguariensis) and Their Contribution to the Total Antioxidant Capacity", Food and Nutrition Sciences, vol. 04, Aug. 1, 2013 (Aug. 1, 2013), pp. 154-162, XP055588480, ISSN: 2157-944X, DOI: 10.4236/fns.2013.48A019.
Marques V. X. and Farah A. (2010) Urinary excretion of chlorogenic acids and metabolites in humans after green mate (I. paraguariensis) consumption. FASEB J. 24, 1, Suppl., [abstract 922.1]. DOI:10.1096/fasebj.24.1_supplement.922.1.
Matsumoto R. L. T., et al. (2009) Effects of maté tea (*Ilex paraguariensis*) ingestion on mRNA expression of antioxidant enzymes, lipid peroxidation, and total antioxidant status in healthy young women. J. Agric. Food Chem. 57, 1775-1780. DOI:10.1021/jf803096g.
Mello F. W., et al. (2018) Maté consumption association with upper aerodigestive tract cancers: a systematic review and meta-analysis. Oral Oncol. 82, 37-47 [plus supplementary data]. DOI:10.1016/j.oraloncology.2018.04.023.
Messina D., et al. (2017) Maté tea and lipid profile in overweight women under caloric restriction. Ann Nutr. Metab. 71, 384 [abstract 144-1131]. DOI:10.1159/000480486.
Miranda D. D. C., et al. (2008) Protective effects of mate tea (Ilex paraguariensis) on H2O2-induced DNA damage and DNA repair in mice. Mutagenesis 23, 261-265. DOI:10.1093/mutage/gen011.
Moura de Oliveira D., et al. (2017) Bioavailability of chlorogenic acids in rats after acute ingestion of maté tea (*Ilex paraguariensis*) or 5-caffeoylquinic acid. Eur. J Nutr. 56, 2541-2556. DOI:10.1007/s00394-016-1290-1.
Rocha D. S., et al. (2018) Effect of yerba mate (Ilex paraguariensis) extract on the metabolism of diabetic rats. Biomed. Pharmacother. 105, 370-376 [plus supplementary figure]. DOI:10.1016/j.biopha.2018.05.132.
Simao Do Carmo L., et al. (2013) The effects of yerba maté (Ilex paraguariensis) consumption on IL-1, IL-6, TNF-α and IL-10 production by bone marrow cells in Wistar rats fed a high-fat diet. Int J Vitam Nutr Res 83, 26-35. DOI:10.1024/0300-9831/a000142.
Sirima Puangpraphant et al: "Dicaffeoylquinic acids in Yerba mate (Ilex paraguariensis St. Hilaire) inhibit NF-&kgr;B nucleus translocation in macrophages and induce apoptosis by activating caspases-8 and -3 in human colon cancer cells", Molecular Nutrition & Food Research, vol. 55, No. 10, Oct. 8, 2011 (Oct. 8, 2011), pp. 1509-1522, XP055175515, ISSN: 1613-4125, DOI: 10.1002/mnfr.201100128.
Souza S. J., et al. (2017) Effect of chocolate and mate tea on the lipid profile of individuals with HIV/AIDS on antiretroviral therapy: A clinical trial. Nutrition 43-44, 61-68. DOI:10.1016/j.nut.2017.06.017.
U.S. FDA (2018) Part 182—Substances generally recognized as safe. Section §182.20—Essential oils, oleoresins (solvent-free), and natural extractives (including distillates). In: U.S. Code of Federal Regulations (CFR). Title 21: Food and Drugs. (U.S. Food and Drug Administration). U.S. Government Printing Office (GPO), Washington, DC.
Vargas Alves R. J., et al. (2008) The evaluation of maté (Ilex paraguariensis) genetic toxicity in human lymphocytes by the

(56) References Cited

OTHER PUBLICATIONS cytokinesis-block in the micronucleus assay. Toxicol. In Vitro 22, 695-698. DOI:10.1016/j.tiv.2007.11.005.
Wnuk M., et al. (2009) Evaluation of the cyto- and genotoxic activity of yerba mate (Ilex paraguariensis) in human lymphocytes in vitro. Mutat. Res. 679, 18-23. DOI:10.1016/j.mrgentox.2009.07.017.
Yara Queiroz et al: The Chlorogenic Acid and Caffeine Content of Verba Mate (Ilex paraguariensis) Beverages11, Jan. 1, 2005 (Jan. 1, 2005), pp. 91-95, XP055715126, Retrieved from the Internet: URL:https://media.enfasis.com/adjuntos/146 /documentos/000/134/0000134821.pdf [retrieved on Jul. 15, 2020].
Yu S., et al. (2015) Yerba mate (Ilex paraguariensis) improves microcirculation of volunteers with high blood viscosity: a randomized, double-blind, placebo-controlled trial. Exp. Gerontol. 62, 14-22 [plus supplementary tables]. DOI:10.1016/j.exger.2014.12.016.
Amazon [online], Aug. 7, 2012 [Retrieval Date: Mar. 28, 2024], Internet: <URL: https://amzn.asia/d/jcWACRC>.
Hariprasad "Cocrystals of Ethenzamide: Study of Structural and Physicochemical Properties", Cryst. Growth Des. 2016; 16: 4473-4481 (Year: 2016).
Kuminek "Cocrystals to facilitate delivery of poorly soluble compounds beyond-rule-of-5", Adv. Drug Deliv. Rev. 2016; 101: 143-166 (Year: 2016).
Naimi, et al., "Rosemary Extract as a Potential Anti-Hyperglycemic Agent: Current Evidence and Future Perspectives", Sep. 1, 2017, Nutrients; vol. 9, Issue 9, pp. 1-19.
Nalte, Yk, et al., Solubility Enhancement of Nevirapine by Cocrystallisation Technique. Journal of Pharmacy Research. Aug. 21, 2015, vol. 9, No. 8; pp. 556-561. ISSN:0974-6943.
Nguyen et al., "Facile preparation of water soluble curcuminoids extracted from turmeric (*Curcuma longa* L.) power by using steviol glucosides," Food Chemistry, 2017, 214, 366-373.
Nicoud, et al., "Estimation of the solubility of metastable polymorphs: A critical review," Cryst. Growth Des., 2018.
Notice of Opposition in EP2934181.
Ohta et al., "Characterization of Novel Steviol Glycosides from Leaves of Stevia rebaudiana Morita," 2010, J. Appl. Glycosci., 57, 199-209.
Prakash Indra et al: "Synthesis and Sensory Evaluation of ent-Kaurane Diterpene Glycosides", Molecules, [Online] vol. 17, No. 8, Jan. 1, 2012 (Jan. 1, 2012), pp. 8908-8916, XP055839039, DOI: 10.3390/molecules17088908 Retrieved from the Internet: URL:https://www.ncbi.nlm.nih.gov/pmc/articles/PMC6268950/pdf/molecules-17-08908.pdf> [retrieved on Aug. 5, 2021].
Prakash, "Characterization and sensory evaluation of a hexa B-D-glucopyranosyl diterpene from Stevia rebaudiana," Natural Products Communications, 2013, 8:1523-1526.
Prakash, et al., "Development of novel functional confectionery using low reduced sugar," Indian Journal of Drugs, 2016, 4(4), 141-148.
Rogers et al., "Changes to the content of sugars, sugar alcohols, myo-inositol, carboxylic acids and inorganic anions in developing grains from different varieties of Robusta (*Coffea canephora*) and Arabica (*C. arabica*) coffees," Plant Science, 1999, 149, 115-123.
Roy, G., "Bitterness: reduction and inhibition," Trends Food Sci Tech, 1992, 3, 85-91.
Schwarz et al., "Investigation of plant extracts for the protection of processed foods against lipid oxidation." Eur Food Res Technol, 2001, 212:319-328.
Shibata et al., "Glucosylation of steviol and steviol-glucosides in extracts from Stevia rebaudiana Bertoni," Plant Physiol., 1991, 95, 152-156.
Shiraishi et al., "Taste-Masking Effect of Chlorogenic Acid (CGA) on Bitter Drugs Evaluated by Taste Sensor and Surface Plasmon Resonance on the Basis of CGA-Drug Interactions," 2017, 65(2):127-133, Chem Pharm Bull (Tokyo).
Standard Method Performance Requirements (SMPRs) for Determination of Phenolic Compounds in Dietary Supplements and Dietary Ingredients Containing Echinacea, Sep. 22, 2017, AOAC International.
Stukelj, et al., "Direct measurement of amorphous solubility," Analytical Chemistry, 2019.
Suarez-Quiroz et al., "Isolation of green coffee chlorogenic acids using activated carbon," Journal of Food Composition and Analysis, 2014, 33:55-58.
SUNUP® Commercially available stevia sweetened green coffee bean beverage, purchased Jun. 2018.
Sweet Drops ™ Liquid Stevia Product, 2012.
Tanaka, O., "Improvement of taste of natural sweeteners," Pure & Appl. Chem., 69(4):975-683, 1997.
Trugo et al., Chlorogenic Acid Composition of Instant Coffees, Analyst, Mar. 1984, vol. 109, pp. 263-266.
Tyrer, D., "The theory of solubility," The Journal of Physical Chemistry, 1912.
Upreti, Mani et al., "Solubility Enhancement of Steviol Glycosides and Characterization of Their Inclusion Complexes with Gamma-Cyclodextrin", Int. J. Mol. Sci. 2011, 12, 7529-7553.
Weidel et al., "A Rapid Method for Quantifying Chlorogenic Acid Levels in Potato Samples," Journal of AOAC International, vol. 97, No. 3, Nov. 3, 2014.
Whole Foods 365 Stevia Extract Liquid, 2012.
Wildermuth et al., "Chlorogenic acid oxidation and its reaction with sunflower proteins to form green-colored complexes," Comprehensive Reviews in Food Science and Food Safety, 2016, vol. 15, 829-843.
Written Opinion of WO 2012/082587, Jun. 13, 2013.
Journal of the Brewing Society of Japan, 1959, vol. 54, No. 4, pp. 239-242.
Liu Na, et al., "Review on Stevia rebaudiana research abroad in 2015", Sugar Crops of China. 2017, 39(1): 57-64.
Moeenfard, et al., "Quantification of Caffeoylquinic Acids in Coffee Brews by HPLC-DAD," Journal of Analytical Methods in Chemistry, Dec. 21, 2014.
Molina-Calle et al., "Development and application of a quantitative method based on LC-QqQ MS/MS for determination of steviol glycosides in Stevia leaves", Talanta 154 (2016) 263-269.
Phenolaeis.com Accessed Sep. 9, 2020 Palm Fruit Bioactives Complex.
Pimpley et al. "The chemistry of chlorogenic acid from green coffee and its role in attenuation of obesity and diabetes" at https://pubmed.ncbi.nim.nih.gov/32633686. (Year: 2020).
Song, "Lenalidomide-Gallic Acid Cocrystals with Constant High Solubility", Crystal Growth & Design, 2015, 15, pp. 4869-4875.
Wang Shaojia, et al., "Progress of functional components in Stevia rebaudiand Bertoni", Science and Technology of Food Industry. 2017, vol. 38, No. 20.
Ana Covarrubias-Cárdenas et al, "Antioxidant Capacity and UPLC-PDA ESI-MS Phenolic Profile of Stevia rebaudiana Dry Powder Extracts Obtained by Ultrasound Assisted Extraction", Agronomy, vol. 8, No. 9, Aug. 31, 2018 (Aug. 31, 2018), p. 170.
Analysis of the chemical constituents of Stevia rebausiana and its sweetness Reb M structure, Mar. 20, 2012, Journal of Beijing University of Chemical Technology (Natural Science).
Anonymous, "Sparkling Organic Grapefruit Ginger Soda", GNPD 2012, retrieved from www.gnpd.comDatabase accession No. 1790955.
Anonymous, "Stevia production process | Cargill no calories sweeteners | Cargill", Nov. 4, 2020 (Nov. 4, 2020), Retrieved from the Internet: URL:https://www.cargill.com/food-beverage/emea/stevia-based-sweeteners-production-process.
Anonymous, "Steviol Glycosides Based Table Sweetener", GNPD14 Dec. 2018 (Dec. 14, 2018), Database accession No. 6205393.
Aranda Gonzalez, et al., "Effect of different drying methods on the composition of steviol glycosides in Stevia rebaudiana Bertoni leaves," Int. Agrophys., 2017, 31, 139-144.
Arthur, R., "'The stevia story has changed!' PureCircle on the evolution of the natural sweetener," Mar. 11, 2019, Beveragedaily.com.
Augustijns and Brewster, "Solvent systems and their selection in pharmaceutics and biopharmaceutics," Springer, 2009.

(56) References Cited

OTHER PUBLICATIONS

Bartoshuk et al., "Sweet Taste of Water Induced by Artichoke," Dec. 1, 1972, Science, 178 (4064), 988-990.
Berte et al. (2011) J. Agric. Food Chem. 59: 5523-5527. (Year: 2011).
Brent, Rhea, "Investigating differences in solubility between crystalline and amorphous forms of pharmaceuticals," AstraZeneca, Mat 2006.
Brittain, Harry, "Thermodynamic vs. kinetic solubility: knowing which is which," American Pharmaceutical Review, 2014.
Chang, et al., "Stability studies of stevioside and Rebaudioside A in carbonated beverages," J. Agric. Food Chem., 1983, 31, 409-412.
Chiou, et al., "A comparison of crystallisation approaches in spray drying," Jounral of Food Engineering, 2008.
Cilliers, et al., "Total polyphenols in apples and ciders; correlation with chlorogenic acid," Journal of Food Science, vol. 55, No. 5, 1990, pp. 1458-1459.
Clifford, "Chlorogenic acids and other cinnamates—nature, occurance, and dietary burden," Journal of the Science of Food and Agriculture, 79:362-372 (1999).
Coquerel, Gerard, "Crystallization of molecular systems from solution: phase diagrams, supersturation, and other basic concepts," Chem Soc Rev, 2014.
Craig et al., "Performance review of a fast HPLC-UV method for the quantification of chorogenic acids in green coffee bean extracts," Talanta, 154 (2016) 481-485.
Crammer and R I Kan B: II Properties and syntheses of sweetening agents, Chemical Society Reviews, Royal Society of Chemistry, UK, vol. 6, Jan. 1, 1977 (Jan. 1, 1977), pp. 431-465, XP009150156, ISSN: 0306-0012 p. 437, paragraph 2-p. 438, paragraph 1.
Cros et al., "Solvent Extraction of Oil and Chlorogenic Acid from Green Coffee Part I: Equilibrium Data," Journal of Food Engineering 10 (1989) 1-11.
Deladino L., et al., "Major phenolics in Yerba mate extracts(Ilex paraguariensis) and their contribution to the total antioxidant capacity," Food and Nutritional Science, 4, 2013.
Douglass, et al., "Kinetics of dissolution of an amorphous solid," J. Phys. Chem. B, 2018.
DuBois, G. E., et al., "Concentration-Response relationship of sweeteners," ACS Syposium Series, 1991.
Edgar Naegele, "Determination of Chlorogenic Acid in Coffee Products According to DIN 10767," Sep. 1, 2016, Agilent Technology, Inc.
Fu et al., "Production of chlorogenic acid and its derivatives in hairy root cultures of Stevia rebaudiana," Jan. 14, 2015, Journal of Agricalatural and Food Chemistry, 63(1):262-268.
Gawel-Beben et al., "Stevia rebuadiana Bert. Leaf extracts as a multifunctional source of natural antioxidants," Molecules, Mar. 27, 2015.
Giordani, Antonio, "The amorphous form in drug development," Crystal Forms, 2012.
Hancock, B. C., et al. "What is the true solubility advantage for amorphous pharmaceuticals?," Pharm Res, 17:397-404, 2000.
Hernandez T et al., "Variations in the phenolic composition of fruit juices with different treatments," European Food Research and Technology, vol. 204, No. 2, 1997, p. 151-155.
Hildebrand, Joel, "Theory of solubility," Physical Review, 1923.
Islam, et al., "Particle crystallization during spray drying in humid air," Journal of Food Engineering, 2010.
Jeon et al., "Contents of chlorogenic acids and caffeine in various coffee-related products," Journal of Advanced Research, 17 (2019), 85-94.
Julia Y.Q. Low et al, "Psychophysical Evaluation of Sweetness Functions Across Multiple Sweeteners", Chemical Senses., vol. 42, No. 2, Oct. 20, 2016 (Oct. 20, 2016), p. 111-120.
Kellie P Burris et al, "Composition and Bioactive Properties of Yerba Mate (Ilex paraguariensis A. St.-Hil.): A Review", Chillan Jun. 2012 (Jun. 2012), p. 268-275.
Kremr et al., "Unremitting Problems with Chlorogenic Acid Nomenclature: A Review," Quim. Nova, vol. 39, No. 4, 530-533, 2016.
Kren, V., et al., "Glycosides in Medicine: The Role of Glycosidic Residue in Biological Activity", Current Medicinal Chemistry, 2001, 8, 1313-1338.
Kroyer, G., "Stevioside and Stevia-sweetener in food: application, stability and interaction with food ingredients," J. Verbr. Lebensm., 2010, 5:225-229.
Ky et al., "Camparison of Five Purification Methods for Chlorogenic Acids in Green Coffee Beans (*Coffea* sp.)," J. Agric. Food Chem. 1997, 45, 786-790, obtained from https://horizon.documentation.ird.fr/exl-doc/pleins_textes/pleins_textes_6/b_fdi_47-48/010010457.pdf.
Lee et al., "Chicoric acid: chemistry distribution, and production," Frontiers in Chemistry, 2013, 1(40).
Liquid Stevia and Liquid Stevia (flavored) from Stevita Co., 2012.
Maietta et al., "Artichoke (*Cynara cardunculus* L. var. *scolymus*) waste as a natural source of carbonyl trapping and antiglycative agents," Food Research International, 100 (2017) 780-790.
Masuda, et al., "Powder Technology Handbook," Taylor & Francis, 2006.
Meilgaard MC, Civille GV, and Carr BT (2007). Sensory Evaluations Techniques, CRC Press, Boca Raton, FL.
Meinhart et al., "Analysis of chlorogenic acids isomers and caffeic acid in 89 herbal infusions (tea)," Journal of Food Composition and Analysis, 73 (2018) 76-82.
Meinhart et al., "Chlorogenic acid isomer contents in 100 plants commercialized in Brazil," Food Research International, 99 (2017) 522-530.
Meireles et al., "Stevia (Stevia rebaudiana Bertoni):—Futuristic view of the sweeter side of life," Floriculture, Omamental and Plant Biotechnology vol. IV, 2006, Global Science Books.
Miura et al., "Molecularly imprinted polymer for chlorogenic acid by modified precipitation polymerization and its application to extraction of chlorogenic acid from Eucommia ulmodies leaves," Journal of Pharmaceutical and Biomedical Analysis, 114 (2015) 139-144.
Murdande, et al., "Aqueous solubility of crytalline and amorphous drugs: challenges in measurement," Pharmaceutical Development and Technology, 2011.
Murdande, et al., "Solubility Advantage of amorphous pharmaceuticals: I. A thremodynamic analysis," Wiley InterScience, 2009.
Murshedkav, Tooba, "Effect of crystalline to amorphous coversion on solubility of cefuroxime axetil," Univeristy of Rhode Island, 2002.
Alibaba ] [Online], "Yerba mate herbal tea", Online available at < <URL:https://japanese.alibaba.com/g/yerba-mate-herbal-tea.html, Dec. 25, 2024, 5 pages.
Alma Japan] [Online], "Yerba Mate Organic Lemon Ginger Tea", Online available at << URL:https://www.almajapan.com/product.asp?CD=MJ0006>, Dec. 25, 2024, 2 pages.
Amazon [Online], May 16, 2018 [search date Dec. 25, 2024], Internet "Balibetov Stainless Steel Double Wall Mate Cup and Bombilla Set—Yerba Mate Set includes 1 Yerba Mate Cup, 2 Bombillas Mate and Brush—Easy Care (Black)", Online Available at << URL:https://amzn.asia/d/3fGkSL6>.

STEVIOL GLYCOSIDE SOLUBILITY ENHANCERS

CROSS-REFERENCE TO RELATED APPLICATIONS

This application is a national phase of International Application No. PCT/US2020/026568, filed Apr. 3, 2020, which claims the benefit of U.S. Application No. 62/830,450, filed Apr. 6, 2019; U.S. Application No. 62/832,062, filed Apr. 10, 2019; U.S. application Ser. No. 16/373,206, filed Apr. 3, 2019, which was published Jul. 25, 2019 as U.S. Patent Application Publication No. 2019/0223481; International Application No. PCT/US2018/054691, filed Oct. 5, 2018; and U.S. Provisional Application No. 62/569,279, filed Oct. 6, 2017. The entirety of each of these applications is hereby incorporated by reference.

FIELD

The present disclosure relates to solubilized steviol glycoside solutions having one or more steviol glycoside compounds and steviol glycoside solubility enhancer, and methods of making and using those solutions. The present disclosure also relates to sweetener compositions and throw syrups to prepare sweetened compositions including food, beverages, dental products, pharmaceuticals, nutraceuticals, and the like.

BACKGROUND

Sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is caloric. Non-caloric or lower caloric sweeteners have been introduced to satisfy consumer demand, and there is desire for these types of sweeteners that have favorable taste characteristics.

*Stevia* is a genus of about 240 species of herbs and shrubs in the sunflower family (Asteraceae), native to subtropical and tropical regions from western North America to South America. The species *Stevia rebaudiana*, commonly known as sweetleaf, sweet leaf, sugarleaf, or simply *stevia*, is widely grown for its sweet leaves. *Stevia*-based sweeteners may be obtained by extracting one or more sweet compounds from the leaves. Many of these compounds are steviol glycoside compounds, which are glycosides of steviol, a diterpene compound. These diterpene glycosides are about 150 to 450 times sweeter than sugar.

Examples of steviol glycoside compounds are described in WO 2013/096420 (see, e.g., listing in FIG. 1); and in Ohta et. al., "Characterization of Novel Steviol Glycosides from Leaves of *Stevia rebaudiana* Morita," J. Appl. Glycosi., 57, 199-209 (2010) (See, e.g., Table 4 at p. 204). Structurally, the diterpene glycosides are characterized by a single base, steviol, and differ by the presence of carbohydrate residues at positions C13 and C19, as presented in FIGS. 2a-2k. See also PCT Patent Publication WO 2013/096420.

Typically, on a dry weight basis, the four major steviol glycoside compounds found in the leaves of *Stevia* are dulcoside A (0.3%), rebaudioside C (0.6-1.0%), rebaudioside A (3.8%) and stevioside (9.1%). Other glycosides identified in *Stevia* extract include one or more of rebaudioside B, D, E, F, G, H, I, J, K, L, M, N, O, steviolbioside and rubusoside.

While the major steviol glycoside Reb A is commonly used as sweetener in beverage applications, it has off-taste issues. More recently, there has been focus on certain minor steviol glycoside compounds which have better taste properties. For example, rebaudioside M has higher sweetness intensity and is more potent than other steviol glycoside compounds (e.g., see Prakash, I., et al. (2013) Nat. Prod. Commun., 8: 1523-1526, and WO 2013/096420). Rebaudioside D tastes about 200-220 times sweeter than sucrose and in a sensory evaluation it had a slow onset of sweetness and was very clean (e.g., see Prakash, I., et al. (2012) Int. J. Mol. Sci., 13:15126-15136).

Rebaudiosides can be challenging to use because they have less than desirable water solubility properties. For example, it has been reported that Reb D is difficult to use in food products because of its low solubility in water at room temperature. For instance, Reb D needs to be heated to near boiling water temperature for 2 hours in order to achieve complete dissolution at 0.8% concentration. At most only 300 to 450 ppm can be solubilized in water at 23° C. (e.g., see US 2013/0251881). As another example, rebaudioside M obtained from *Stevia rebaudiana* has poor aqueous solubility and dissolution qualities in beverage formulations (e.g., see US 2014/0171519).

SUMMARY

The present disclosure generally relates to solubilized steviol glycoside compositions, e.g., aqueous solutions, having one or more steviol glycoside compounds and one or more steviol glycoside solubility enhancer compounds. The disclosure also relates to uses of the solubilized steviol glycoside compositions as sweetener compositions, which may be used to prepare sweetened compositions including food, beverages, and other similar products.

DETAILED DESCRIPTION

This disclosure relates generally to steviol glycoside solubility enhancers. For example, some aspects of this disclosure are directed to compositions, e.g., a sweetener composition, a beverage, or a food product including steviol glycoside and steviol glycoside solubility enhancer to enhance solubility of the steviol glycoside.

If it is desired to provide steviol glycosides and steviol glycoside solubility enhancers in enriched or purified form, or where steviol glycoside solubility enhancer compounds are separated from steviol glycoside compounds, or separated from one another, further purification can be carried out. Such enrichment or purification of steviol glycoside compounds and steviol glycoside solubility enhancer compounds can be carried out on liquid fermentation media, or the fermentation media can then be dried down prior to purification. For example, fermentation media can be dried down using lyophilization to form a dry composition (e.g., powder or flakes) including steviol glycoside compounds and one or more of steviol glycoside solubility enhancers that can be subsequently processed.

As the term is used herein, "steviol glycoside" generally refers to the total content of steviol glycoside compounds. The weight of a steviol glycoside is determined on a dry (anhydrous) basis. Unless expressed herein otherwise, an "amount" of steviol glycoside will refer to the percentage by weight (% wt) of the total content of steviol glycoside compounds.

As discussed herein, sweetener compositions include steviol glycoside and steviol glycoside solubility enhancer, as well as other compounds. Steviol glycoside compounds generally have the formula

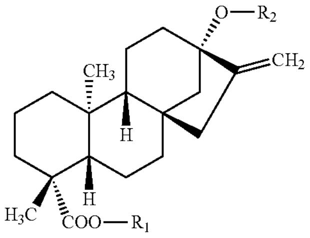

wherein steviol ($R_1$ and $R_2$=H) is the aglycone backbone and $R_1$ and $R_2$ can each be hydrogen or one or more sugar moieties. These sugar moieties are most commonly glucose, rhamnose, or xylose, but steviol glycoside compounds have been reported that include fructose and deoxyglucose sugar moieties.

Exemplary steviol glycoside compounds that may be useful in solutions described herein include one or more of Rebaudioside A (Reb A) (CAS #58543-16-1), Rebaudioside B (Reb B) (CAS #58543-17-2), Rebaudioside C (Reb C) (CAS #63550-99-2), Rebaudioside D (Reb D) (CAS #63279-13-0), Rebaudioside E (Reb E) (CAS #63279-14-1), Rebaudioside F (Reb F) (CAS #438045-89-7), Rebaudioside M (Reb M) (CAS #1220616-44-3), Rubusoside (CAS #63849-39-4), Dulcoside A (CAS #64432-06-0), Rebaudioside I (Reb I) (MassBank Record: FU000332), Rebaudioside Q (Reb Q), Rebaudioside 0 (Reb 0), Rebaudioside N (Reb N) (CAS #1220616-46-5), 1,2-Stevioside (CAS #57817-89-7), 1,3-Stevioside (Reb G), Steviol-1,2-Bioside (MassBank Record: FU000299), Steviol-1,3-Bioside, Steviol-13-O-glucoside (13-SMG), Steviol-19-O-glucoside (19-SMG), and steviol glycoside compounds having 1, 2, 3, 4, 5, 6, 7, 8, 9, 10 or sugar additions (e.g., glucose, rhamnose, and/or xylose), and isomers thereof. See, e.g., Steviol Glycosides Chemical and Technical Assessment 82nd JECFA, 2016, revised by Jeff Moore, Food Agric. Org.

Exemplary steviol glycoside compounds can include rebaudioside M, rebaudioside D, rebaudioside A, rebaudioside B, rebaudioside J, rebaudioside N, and/or rebaudioside O. In some aspects, one or more of the steviol glycoside compounds are produced by enzymatic modification or by fermentation by an engineered microorganism. For example, rebaudioside D and M can be produced by an engineered organism and then isolated to produce a steviol glycoside of primarily rebaudioside D and rebaudioside M as the predominant steviol glycoside species. In some aspects, one or more of the steviol glycoside compounds are isolated from *Stevia rebaudiana.*

In some aspects, the steviol glycoside can comprise rebaudioside D and rebaudioside M in an amount greater than other steviol glycoside compounds. For example, rebaudioside M and/or rebaudioside D can be present in the steviol glycoside in a total amount of about 75 percent by weight ("% (wt)" or "wt %") or greater, about 80% (wt) or greater, about 80% (wt) or greater, preferably about 90% (wt) or greater, about 92.5% (wt) or greater, or 95% (wt) or greater, of a total amount steviol glycoside compounds in the composition. Rebaudioside M can be the predominant steviol glycoside compound in the composition, and can be present, for example, in an amount in the range of about 45% (wt) to about 70% (wt), about 50% (wt) to about 65% (wt), or about 52.5% (wt) to about 62.5% (wt) of the total amount steviol glycoside compounds in the composition. Rebaudioside D can be in an amount less than Rebaudioside M, such as in an amount in the range of about 25% (wt) to about 50% (wt), about 30% (wt) to about 45% (wt), or about 32.5% (wt) to about 42.5% (wt) of the total amount steviol glycoside compounds in the composition.

The steviol glycoside can optionally include lesser amounts of steviol glycoside compounds other than rebaudioside D and rebaudioside M. For example, the steviol glycoside can include one or more of rebaudioside A, rebaudioside B, or stevioside in an amount of about 1% (wt) or less, about 0.5% (wt) or less, or about 0.25% (wt) or less, of a total amount steviol glycoside compounds in the composition.

Beneficially, it has been found that certain steviol glycoside solubility enhancer compounds can improve solubility of steviol glycoside in an aqueous solution, and therefore compositions can be prepared having a greater concentration of steviol glycoside. As used herein "instantaneous solubility" refers to the solubility of a steviol glycoside compound, or mixture of steviol glycoside compounds, that are vigorously mixed with water at room temperature (25° C.). As used herein "equilibrium solubility" refers to the solubility of a steviol glycoside compound, or mixture of steviol glycoside compounds, that are vigorously mixed with deionized water at 80° C. for 15 minutes, cooled to room temperature (25° C.), and then observed at least four days. Clear solutions without precipitates are considered soluble. Unless indicated otherwise herein, the term "solubility" refers to "equilibrium solubility."

In the absence of compounds that enhance solubility, rebaudioside D has a very low instantaneous solubility (less than 0.08% at room temperature) in water. Upon heating to 80° C. for 15 minutes, rebaudioside D has an equilibrium solubility of 0.08% for at least four days at room temperature. Rebaudioside M has a higher solubility than rebaudioside D. The instantaneous solubility of rebaudioside M is about 0.13%, and its equilibrium solubility is about 0.2% at room temperature.

The presence of steviol glycoside solubility enhancer can improve the solubility of steviol glycoside by 1, 2, 3, 4, 5, 10, 15, 20, 50, 100, 200, or 250 times, or more.

In some modes of practice, a steviol glycoside solubility enhancer can be enriched in a composition. The term "enriched" refers to an increase in the amount of one or more steviol glycoside solubility enhancer compounds relative to one or more other compounds that are present in a composition. A composition that is enriched for one or more steviol glycoside solubility enhancer compounds can be combined with a steviol glycoside to improve solubility of the steviol glycoside.

In yet other modes of practice, one or more steviol glycoside solubility enhancer compounds are purified from *stevia* extract to provide a composition comprising steviol glycoside solubility enhancer that is essentially free of other components found in *stevia* leaves, such as those listed in Tables 2-6. Such a purified composition can be combined with steviol glycoside, increasing the aqueous solubility of the steviol glycoside to form a composition with higher steviol glycoside concentration.

Accordingly, other aspects of the disclosure provide a method of enhancing the solubility of steviol glycoside in an aqueous composition comprising a step of providing an aqueous composition comprising steviol glycoside solubility enhancer and steviol glycoside, e.g., rebaudioside A, rebaudioside B, rebaudioside M, rebaudioside D, rebaudioside I, rebaudioside J, rebaudioside Q, rebaudioside N, rebaudioside 0, or stevioside, or any combination thereof. For example, the steviol glycoside can be added to a composition that has the steviol glycoside solubility enhancer, the steviol glycoside and the steviol glycoside solubility enhancer may be mixed, or the steviol glycoside solubility enhancer can be added to a composition having the steviol glycoside.

Sweetener compositions (also referred to as sweetening compositions), as used herein, refers to compositions that include steviol glycoside and steviol glycoside solubility enhancer. Thus, one or more steviol glycoside compound(s) such as Reb B, Reb M and/or Reb D can be present in a greater amount in the composition, such as greater than about 75%, greater than about 80%, greater than about 85%, greater than about 90%, greater than about 95%, or greater than about 99% of the total amount of steviol glycoside in the composition. As a practical matter, it may be useful to include at least 0.5% of other steviol glycosides to avoid undue processing costs.

In one aspect, steviol glycoside solubility enhancer is present in a sweetener composition at a molar ratio of steviol glycoside to steviol glycoside solubility enhancer of about 1:1, 1:0.9, 1:0.8, 1:0.7, 1:0.6, 1:0.5, 1:0.4, 1:0.3, 1:0.2, or 1:0.1. In one aspect, steviol glycoside solubility enhancer is present in a sweetener composition at a molar ratio of steviol glycoside to steviol glycoside solubility enhancer of about 1:1, 1:2, 1:3, 1:4, 1:5, 1:6, 1:7, 1:8, 1:9, or 1:10.

The sweetener composition can optionally include another sweetener, an additive, a liquid carrier, or combinations thereof. Sweetener compositions are used to sweeten other compositions (sweetenable compositions) such as foods, beverages, medicines, oral hygiene compositions, nutraceuticals, and the like.

Sweetenable compositions, as used herein, mean substances which are contacted with the mouth of man or animal, including substances which are taken into but subsequently ejected from the mouth (such as a mouthwash rinse) and substances which are drunk, eaten, swallowed or otherwise ingested, and are suitable for human or animal consumption when used in a generally acceptable range. Sweetenable compositions are precursor compositions to sweetened compositions and are converted to sweetened compositions by combining the sweetenable compositions with at least one sweetening composition and optionally one or more other sweetenable compositions and/or other ingredients.

Sweetened compositions, as used herein, mean substances that are derived from constituents including at least one sweetenable composition and at least one sweetener composition. In some modes of practice, a sweetened composition may be used itself as a sweetening composition to sweeten still yet further sweetenable compositions. In some modes of practice, a sweetened composition may be used as a sweetenable composition that is further sweetened with one or more additional sweetening compositions. For example, a beverage with no sweetener component is a type of sweetenable composition. A sweetener composition can be added to the un-sweetened beverage, thereby providing a sweetened beverage. The sweetened beverage is a type of sweetened composition.

In some preparations, steviol glycoside provides the sole sweetener component in a sweetening composition.

In some aspects, a sweetening composition comprises steviol glycoside in an amount effective to provide a sweetness strength equivalent to a specified amount of sucrose. The amount of sucrose in a reference solution may be described in degrees Brix (° Bx). One degree Brix is 1 gram of sucrose in 100 grams of solution and represents the strength of the solution as percentage by weight (% w/w). For example, a sweetener composition contains steviol glycoside in an amount effective to provide a sweetness equivalent from about 0.50 to 14 degrees Brix of sugar when present in a sweetened composition, such as, for example, from about 5 to about 11 degrees Brix, from about 4 to about 7 degrees Brix, or about 5 degrees Brix.

The amount of steviol glycoside in the sweetener composition may vary. Steviol glycoside can be present in a sweetener composition in any amount to impart the desired sweetness when the sweetener composition is incorporated into a sweetened composition. For example, Reb M and/or Reb D are present in the sweetener composition in an amount effective to provide total steviol glycoside concentration from about 1 ppm to about 10,000 ppm (1% (wt)), to about 100,000 ppm (10% (wt)), when present in a sweetened composition, In another aspect, the steviol glycoside is present in the sweetener composition in an amount effective to provide a steviol glycoside concentration in the range of about 10 ppm to about 1,000 ppm, more specifically about 10 ppm to about 800 ppm, about 50 ppm to about 800 ppm, about 50 ppm to about 600 ppm, or about 200 ppm to about 500 ppm.

In one aspect, steviol glycoside compounds other than Reb D, Reb M, Reb G, Reb O, Reb N, and/or Reb E, or other than Reb D, Reb M, Reb B and/or Reb A, or other than Reb D and/or Reb M, are present in a sweetened composition at about 0.05 to 70 wt % of the total content of the sweetener composition; e.g., about 0.1 to 50, 0.5 to 70, 1 to 50, 1 to 35, 2 to 25, 3 to 20, 5 to 15, 0.1 to 15, 0.5 to 10, 1 to 5%, etc. In one aspect, steviol glycoside compounds other than Reb D, Reb M, Reb G, Reb O, Reb N, and/or Reb E, or other than Reb D, Reb M, Reb B and/or Reb A or other than Reb D and/or Reb M, are at a weight ratio of the total of all other glycosides of 1:1 to 1:20, 1:1.5 to 1:15, 1:2 to 1:10, 1:2.5 to 1:7.5, or 1:3 to 1:5, in a sweetened composition.

Unless otherwise expressly stated, ppm is on a weight basis.

In some aspects, a sweetener composition having the steviol glycoside and steviol glycoside solubility enhancer, also contain one or more additional non-steviol glycoside sweetener compound(s). The non-steviol glycoside sweetener compounds can be any type of sweetener, for example, a sweetener obtained from a plant or plant product, or a physically or chemically modified sweetener obtained from a plant, or a synthetic sweetener.

For example, exemplary non-steviol glycoside sweeteners include sucrose, fructose, glucose, erythritol, maltitol, lactitol, sorbitol, mannitol, xylitol, tagatose, trehalose, galactose, rhamnose, cyclodextrin (e.g., a-cyclodextrin, β-cyclodextrin, and γ-cyclodextrin), ribulose, threose, arabinose, xylose, lyxose, allose, altrose, mannose, idose, lactose, maltose, invert sugar, isotrehalose, neotrehalose, palatinose or isomaltulose, erythrose, deoxyribose, gulose, idose, talose, erythrulose, xylulose, psicose, turanose, cellobiose, glucosamine, mannosamine, fucose, fuculose, glucuronic acid, gluconic acid, glucono-lactone, abequose, galactosamine, xylo-oligosaccharides (xylotriose, xylobiose and the like), gentio-oligoscaccharides (gentiobiose, gentiotriose, gentiotetraose and the like), galacto-oligosaccharides, sorbose, ketotriose (dehydroxyacetone), aldotriose (glyceraldehyde), nigero-oligosaccharides, fructooligosaccharides (kestose, nystose and the like), maltotetraose, maltotriol, tetrasaccharides, mannan-oligosaccharides, malto-oligosaccharides (maltotriose, maltotetraose, maltopentaose, maltohexaose, maltoheptaose and the like), dextrins, lactulose, melibiose, raffinose, rhamnose, ribose, isomerized liquid sugars such as high fructose corn/starch syrup (HFCS/HFSS) (e.g., HFCS55, HFCS42, or HFCS90), coupling sugars, soybean oligosaccharides, glucose syrup and combinations thereof. D- or L-configurations can be used when applicable.

The steviol glycoside and carbohydrate sweetener may be present in any weight ratio, such as, for example, from about 1:14,000 to about 100:1, such as, for example, about 1:100. Carbohydrates are present in the sweetener composition in an amount effective to provide a concentration from about 100 ppm to about 140,000 ppm when present in a sweetened composition, such as, for example, a beverage.

In other aspects, the sweetener composition including the steviol glycoside and steviol glycoside solubility enhancer, additionally include one or more synthetic sweeteners. In one aspect, a synthetic has a sweetness potency greater than sucrose, fructose, and/or glucose, yet has less calories than sucrose, fructose, and/or glucose. Exemplary synthetic non-steviol glycoside sweeteners include sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, and combinations thereof. In aspects where the sweetener composition includes the steviol glycoside and synthetic sweetener, the synthetic sweetener can be present in an amount effective to provide a concentration from about 0.3 ppm to about 3,500 ppm when present in a sweetened composition, such as, for example, a beverage.

The sweetener compositions can be customized to provide a desired calorie content. For example, sweetener compositions can be "full-calorie", such that they impart the desired sweetness when added to a sweetenable composition (such as, for example, a beverage) and have about 120 calories per 8 oz serving. Alternatively, sweetener compositions can be "mid-calorie", such that they impart the desired sweetness when added to a sweetenable composition (such as, for example, as beverage) and have less than about 60 calories per 8 oz serving. In other aspects, sweetener compositions can be "low-calorie", such that they impart the desired sweetness when added to a sweetenable composition (such as, for example, as beverage) and have less than 40 calories per 8 oz serving. In still other aspects, the sweetener compositions can be "zero-calorie," such that they impart the desired sweetness when added to a sweetenable composition (such as, for example, a beverage) and have less than 5 calories per 8 oz. serving. Non-calorie compositions are "non-nutritive." In some aspects, low calorie compositions can also be referred to as "non-nutritive."

The weight ratio of the total amount of sweetener compositions used to sweeten a sweetened composition can vary over a wide range. In many aspects, this weight ratio is in the range from 1:10,000 to 10:1.

Sweetener compositions having steviol glycoside and steviol glycoside solubility enhancer can be incorporated in any known edible material (referred to herein as a "sweetenable composition") or other composition intended to be ingested and/or contacted with the mouth of a human or animal, such as, for example, pharmaceutical compositions, edible gel mixes and compositions, dental and oral hygiene compositions, foodstuffs (confections, condiments, chewing gum, cereal compositions, baked goods, baking goods, cooking adjuvants, dairy products, and tabletop sweetener compositions), beverages, and other beverage products (e.g., beverage mixes, beverage concentrates, etc.).

In one aspect, a sweetened composition is derived from ingredients comprising a sweetenable composition and a composition having steviol glycoside and steviol glycoside solubility enhancer. In another aspect, the sweetened composition is derived from ingredients comprising a sweetener composition comprising steviol glycoside and steviol glycoside solubility enhancer. The sweetened compositions can optionally include one or more additives, liquid carriers, binders, sweeteners, functional ingredients, other adjuvants, and combinations thereof.

Suitable "bulking agents" include, but are not limited to, maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, in accordance with still other aspects, granulated sugar (sucrose) or other caloric sweeteners such as crystalline fructose, other carbohydrates, or sugar alcohol can be used as a bulking agent due to their provision of good content uniformity without the addition of significant calories.

The tabletop sweetener compositions can be packaged in any form known in the art. Non-limiting forms include, but are not limited to, powder form, granular form, packets, tablets, sachets, pellets, cubes, solids, and liquids. The amount of steviol glycoside in a dry-blend tabletop sweetener formulation can vary. In a particular aspect, a dry-blend tabletop sweetener formulation may contain steviol glycoside in an amount from about 1% (wt) to about 10% (wt) of the tabletop sweetener composition.

A tabletop sweetener composition also may be embodied in the form of a liquid, wherein a sweetener composition comprising steviol glycoside and including steviol glycoside solubility enhancer, is combined with a liquid carrier. Suitable non-limiting examples of carrier agents for liquid tabletop functional sweeteners include water, alcohol, polyol, glycerin base or citric acid base dissolved in water, and mixtures thereof.

In one aspect, the sweetened composition is a beverage product comprising steviol glycoside and including steviol glycoside solubility enhancer. As used herein a "beverage product" is a ready-to-drink beverage, a beverage concentrate, a beverage syrup, frozen beverage, or a powdered beverage. Suitable ready-to-drink beverages include carbonated and non-carbonated beverages. Carbonated beverages include, but are not limited to, enhanced sparkling beverages, cola, lemon-lime flavored sparkling beverage, orange flavored sparkling beverage, grape flavored sparkling beverage, strawberry flavored sparkling beverage, pineapple flavored sparkling beverage, ginger-ale, soft drinks and root beer. Non-carbonated beverages include, but are not limited to fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, cafe au lait, milk tea, fruit milk beverages), beverages containing cereal extracts, smoothies and combinations thereof.

Beverage concentrates and beverage syrups can be prepared with an initial volume of liquid matrix (e.g. water) and the desired beverage ingredients. Full strength beverages are then prepared by adding further volumes of water. Powdered beverages are prepared by dry-mixing all of the beverage ingredients in the absence of a liquid matrix. Full strength beverages are then prepared by adding the full volume of water.

Beverage products may be non-alcoholic. Non-alcoholic beverage products contain less than 0.5% (wt), preferably less than 0.2% (wt), less than 0.1% (wt), or less than 0.05% (wt) of ethanol. More broadly, non-alcoholic beverage products may contain less than 0.5% (wt), preferably less than 0.2% (wt), less than 0.1% (wt), or less than 0.05% (wt) of C1-C4 alcohols (e.g., methanol, ethanol, propanol, butanol, etc.). Many non-alcoholic beverage products are alcohol-free, i.e., do not contain ethanol or do not contain C1-C4 alcohols. Non-alcoholic beverages may, however, include other alcohols, e.g., sugar alcohols such as erythritol, isomalt, xylitol, glycerol, sorbitol, mannitol, maltitol, lactitol, and inositol. A commercially useful ready-to-drink beverage or beverage concentrate is ethanol-free and includes water, steviol glycoside solubility enhancer, and a sugar alcohol. Such a commercially useful beverage product may also include steviol glycoside.

In one aspect, a beverage contains steviol glycoside and steviol glycoside solubility enhancer. Any sweetener composition comprising steviol glycoside and steviol glycoside solubility enhancer detailed herein can be used in the beverages. In another aspect, a method of preparing a beverage comprises combining a liquid matrix, steviol glycoside and steviol glycoside solubility enhancer. The method can further comprise addition of one or more sweeteners, additives and/or functional ingredients. In still another aspect, a method of preparing a beverage comprises combining a liquid matrix and a sweetener composition comprising steviol glycoside and steviol glycoside solubility enhancer.

In another aspect, a beverage contains a sweetener composition containing steviol glycoside, wherein the steviol glycoside is present in the beverage in an amount ranging from about 1 ppm to about 10,000 ppm, such as, for example, from about 25 ppm to about 800 ppm. In another aspect, steviol glycoside is present in the beverage in an amount ranging from about 100 ppm to about 600 ppm. In yet other aspects, steviol glycoside is present in the beverage in an amount ranging from about 100 to about 200 ppm, from about 100 ppm to about 300 ppm, from about 100 ppm to about 400 ppm, or from about 100 ppm to about 500 ppm. In still another aspect, steviol glycoside is present in the beverage in an amount ranging from about 300 to about 700 ppm, such as, for example, from about 400 ppm to about 600 ppm. In a particular aspect, steviol glycoside is present in the beverage in an amount of about 500 ppm.

In one aspect, the composition is a beverage and the steviol glycoside content in the beverage is about 50 to 1500 ppm, or 100 to 1200 ppm, 200 to 1000 ppm, 300 to 900 ppm, 350 to 800 ppm, 400 to 600 ppm, or 450 to 550 ppm. In one aspect, steviol glycoside compounds other than Reb D, Reb M, Reb B and/or Reb A, or other than Reb D and/or Reb B, and optionally other than Reb G, Reb J, Reb O, Reb N, and/or Reb E, are present in a beverage at about at least 1 ppm to about 600 ppm, e.g., about 50 ppm to about 500 ppm, including at least 1, 5, 10, 20, 30, 40, 50, 125, 150, 150, 175, or 200 ppm. In one aspect, steviol glycoside compounds other than Reb D, Reb M, Reb B and/or Reb A, or other than Reb D and/or Reb B, and optionally other than Reb G, Reb O, Reb N, and/or Reb E, are present in a beverage at about 1 to 600 ppm 10 to 400, 50 to 200, 75 to 150, 5 to 200, 10 to 100, 20 to 90, or 30 to 80 ppm. In one aspect, steviol glycoside compounds other than Reb D, Reb M, Reb B and/or Reb A, are present in a beverage at about 1 to 600 ppm 10 to 400, 50 to 200, 75 to 150, 5 to 200, 10 to 100, 20 to 90, or 30 to 80 ppm.

Exemplary Natural Sources of Steviol Glycoside Solubility Enhancers

Steviol glycoside solubility enhancers may be prepared synthetically or isolated from organisms including but not limited to plants, e.g., plant leaves and stems. The following Table provides genera of plants that are examples of plants likely to contain compounds within the scope of the disclosed steviol glycoside solubility enhancers, e.g., formula (I), including for instance caffeic acid, chlorogenic acid, cynarin, and/or structurally-related compounds which likely aid in the solubility of steviol glycoside.

TABLE 1

| Genus | Exemplary species and synonymous species (Syn.) | Exemplary common names |
|---|---|---|
| *Stevia* | *rebaudiana* | Stevia |
| *Siraitia* | *grosvenorii* | Monkfruit |
| *Coffea* | *C. arabica, C. canephora, C. ambongensis, C. boinensis, C. labatii, C. pterocarpa, C. bissetiae, C. namorokensis, C. charrieriana, C. anthonyi* | Coffee, Coffee beans, Green coffee beans |
| *Camellia* | *C. sinensis, C. japonica, C. sasanqua, C. oleifera, C. crapnelliana, C. reticulata, C. cuspidata, C. saluenensis, Camellia* × *williamsii, C. taliensis, C. rusticana* | Tea, White tea, Yellow tea, Green tea, Oolong tea, Black tea, Red tea, Post-fermented tea |
| *Phyllostachys* | *P. edulis,* Syn. *Bambos moosoo,* Syn. *Bambusa heterocycle,* Syn. *Bambusa mitis,* Syn. *Bambusa pubescens, P. bicolor, P. heterocycla, P. pubescens* | Bamboo, moso bamboo, tortoise-shell bamboo, mao zhu |
| *Calluna* | *C. vulgaris* | common heather, ling, heather |
| *Helianthus* | *H. annuus, H. tuberosus, H. verticillatus, H. giganteus, H. petiolaris,* | Sunflower, Sunflower seeds |
| *Vaccinium* | *V. corymbosum, V. alaskaense, V. angustifolium, V. crassifolium, V. boreale, V. darrowii, V. koreanum, V. myrtillus, V. uliginosum, V. macrocarpon, V. oxycoccos, V. ovatum, V. uliginosum, V. vitis-idaea* | Blueberries, cranberries, bilberries, grouseberries, whortleberry, lingonberry, cowberry, huckleberry |
| *Vitis* | *Vitis vinifera* | Grapes, Wine, Raisins |
| *Cichorium* | *Cichorium intybus* | Chicory |
| *Echinacea* | *E. purpurea, E. angustifolia* | Eastern purple coneflower, Echinacea |

TABLE 1-continued

| Genus | Exemplary species and synonymous species (Syn.) | Exemplary common names |
| --- | --- | --- |
| *Parietaria* | *Parietaria officinalis* | Eastern pellitory-of-the-wall, Upright pellitory, Lichwort |
| *Chelidonium* | *Chelidonium majus* | Greater celandine, Tetterwort, Nipplewort, Swallowwort |
| *Sanguinaria* | *Sanguinaria canadensis* | Bloodroot |
| *Urtica* | *Urtica dioica* | Common nettle, Stinging nettle |
| *Solanum* | *S. tuberosum, S. stenotomum, S. phureja, S. goniocalyx, S. ajanhuiri, S. chaucha, S. juzepczukii, S. melongena, S. lycopersicum, S. incanum,* Syn. *Lycopersicon esculentum* | Potato, Potato leaves, Eggplant, Aubergine, Tomato, Cherry tomato, Bitter apple, Thorn apple |
| *Ipomoea* | *Ipomoea batatas* | Sweet potato |
| *Malus* | *Malus pumila, Malus domestica* | Apple, Apple juice |
| *Prunus* | *P. persica, P. dulcis, P. amygdalus, P. avium, P. cerasus, P. domestica, P. salicina* | Peach, Nectarine, Cherry, Sour cherry, Wild cherry, Apricot, Almond, Plum, Prune |
| *Ilex* | *I. paraguariensis, I. guayusa, I. kudingcha, I. vomitoria, I. aquifolium, I. latifolia, I. opaca* | Holly, Yerba mate, Mate, Guayusa, Yaupon Holly, Kuding |
| *Paullinia* | *Paullinia cupana* | Guarana |
| *Theobroma* | *Theobroma cacao* | Cocoa, Cocoa bean, Cacao, Cacao bean |
| *Cola* | *C. acuminata, C. Cola nitida, C. elegans, C. reticulate, C. nigerica, C. umbratilis* | Kola nut, Kola tree, Cola nut, Cola tree |
| *Matteuccia* | *M. struthiopteris, M. orientalis, M. intermedia,* | Ostrich fern, Oriental ostrich fern, Fiddlehead fern, Shuttlecock fern |
| *Pentarhizidium* | *Pentarhizidium orientalis* | Oriental ostrich fern |
| *Osmunda* | *Osmunda japonica, Osmunda regalis* | Asian royal fern, Royal fern |
| *Pteridium* | *Pteridium aquilinum* | Bracken, Brake, Common bracken, Eagle fern, Eastern brakenfern |
| *Syzygium* | *Syzygium aromaticum* | Clove |
| *Cinnamomum* | *C. verum, C. cassia, C. tamala* | Cinnamon, Indian bay leaf |
| *Myristica* | *M. fragrans, M. argentea, M. malabarica* | Nutmeg |
| *Laurus* | *Laurus nobilis* | Bay laurel, Bay leaf |
| *Ocimum* | *Ocimum basilicum* | Basil, Great basil, Saint-Joseph's-wort |
| *Thymus* | *Thymus vulgaris* | Thyme |
| *Salvia* | *Salvia officinalis* | Sage, Garden sage, Common sage, Culinary sage |
| *Rosmarinus* | *Rosmarinus officinalis* | Rosemary |
| *Origanum* | *O. vulgare, O. majorana,* Syn. *Majorana hortensis,* Syn. *Majorana majorana, O. onites, O. pulchellum* | Oregano, Wild marjoram, Marjoram, Sweet marjoram, Knotted marjoram, Pot marjoram |
| *Anethum* | *Anethum graveolens* | Dill |
| *Pimpinella* | *Pimpinella anisum* | Anise |
| *Illicium* | *Illicium verum* | Star anise |
| *Foeniculum* | *Foeniculum vulgare* | Fennel, Florence fennel |
| *Artemisia* | *Artemisia dracunculus, Artemisia vulgaris* | Tarragon, Estragon, Mugwort |
| *Glycyrrhiza* | *Glycyrrhiza glabra* | Licorice, Liquorice |
| *Glycine* | *Glycine max* | Soy, Soybean, Soyabean, Soya bean |
| *Triticum* | *Triticum aestivum,* | Wheat, Common wheat |
| *Olyza* | *Olyza sativa, Olyza glaberrima* | Rice |
| Brassica | *B. napus, B. rapa, B. campestres, B. juncea, B. oleracea* | Canola, Broccoli, Cauliflower, Cabbage, Bok choy, Kale, Collard greens, Brussels sprouts, Kohlrabi |
| *Drimys* | *Drimys winteri* | Winter's bark |
| *Sambucus* | *Sambucus nigra* | Elderflower |
| *Boehmeria* | *Boehmeria caudata* | Assa-Peixe |
| *Cynara* | *Cynara scolymus* | Artichoke |
| *Arctium* | *Arctium lappa* | Greater burdock |
| *Valeriana* | *Valeriana officinalis* | Valerian |
| *Matricaria* | *Matricaria chamomilla* | Chamomile |
| *Strychnos* | *Strychnos nux-vomica* | strychnine tree, nux vomica, poison nut, semen strychnos, quaker buttons |

In some aspects, the steviol glycoside solubility enhancer may be isolated from botanical sources, such as those set forth in Table 1. Examples of commercially useful botanical sources from which steviol glycoside solubility enhancers may be isolated include yerba mate plant (*Ilex paraguariensis*), *stevia*, coffee, tea, chicory, and globe artichoke. Some botanical sources may produce steviol glycoside solubility enhancer that is enriched for one or more of caffeic acid, monocaffeoylquinic acids, and dicaffeoylquinic acids and can increase solubility of steviol glycoside composition. For example, steviol glycoside solubility enhancer isolated from yerba mate plant may be enriched for dicaffeoylquinic acids and can increase solubility of the steviol glycoside composition. In other aspects, steviol glycoside solubility enhancer isolated from yerba mate plant that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

Steviol glycoside solubility enhancers may be isolated in a variety of ways. Some suitable processes are disclosed in more detail in U.S. Provisional Application Ser. No. 62/676,722, filed May 25, 2018, and entitled "Methods for Making Yerba Mate Extract Composition." For example, steviol glycoside solubility enhancer may be isolated from a botanical source that comprises one or more of monocaffeoylquinic acid, dicaffeoylquinic acid, and salts thereof. For example, yerba mate biomass and *stevia* biomass can be used to prepare steviol glycoside solubility enhancer. In one exemplary process, steviol glycoside solubility enhancer is prepared from commercially obtained comminuted yerba mate biomass. Briefly, yerba mate biomass is suspended in 50% (v/v) ethanol/water, shaken for at least 1 hour, and the resulting mixture filtered to obtain an initial extract. The initial extract is diluted to 35% (v/v) ethanol with water and refiltered. Refiltered permeate is then applied to a column of AMBERLITE® FPA 53 resin that has been equilibrated in 35% (v/v) ethanol/water and the column permeate is discarded. The column is washed with 35% (v/v) ethanol/water and the column permeate is discarded. The column is then eluted with 10% (w/v) FCC grade sodium chloride in 50% (v/v) ethanol/water and the eluent retained. Nitrogen gas is blown at room temperature over a surface of the eluent to remove ethanol and reduce the eluent to ⅓ of its original volume. The reduced volume eluent is then filtered through a 0.2 μm polyethersulfone filter and then decolored by passing through a 3 kDa molecular weight cutoff membrane. The decolored permeate is retained and desalted by passing through a nanofiltration membrane. The desalted permeate is then freeze-dried to obtain the steviol glycoside solubility enhancer. This process is also suitable to obtain steviol glycoside solubility enhancer from *stevia* biomass and can be adapted to obtain steviol glycoside solubility enhancer from other botanical sources.

Some compounds can adversely impact flavor or aroma of an aqueous solution or a modified steviol glycoside solution. Certain steviol glycoside solubility enhancers, such as those prepared from a plant extract do not include one or more of the compounds shown in Table 2, or any combination thereof, above the disclosed preferred content levels. All preferred content levels are stated as weight percentage on a dry weight basis. Certain commercially desirable solid (dry) steviol glycoside solubility enhancers do not include more than the preferred content level of any of the compounds listed in Table 2. For those compounds listed that are acids, the compound may be present in acid form and/or in salt form.

TABLE 2

| Class of compounds | Preferred Content Level (% wt) | % wt of compounds in steviol glycoside solubility enhancer solid (dry) compositions |
|---|---|---|
| Organic acids | <3%, preferably <2%, <1%, or 0% | malonate, malonic acid, oxalate, oxalic acid, lactate, lactic acid, succinate, succinic acid, malate, malic acid, citrate, citric acid |
| | <0.5%, preferably <0.25% or 0% | tartrate, tartaric acid, pyruvate, pyruvic acid, fumarate, fumaric acid, ascorbic acid, sorbate, sorbic acid, acetate, acetic acid |
| Inorganic acids | <1%, preferably <0.5% or 0% | sulfate, sulfuric acid, phosphate, phosphoric acid, nitrate, nitric acid, nitrite, nitrous acid, chloride, hydrochloric acid, ammonia, ammonium |
| Flavanoids, isoflavanoids, and neoflavanoids | <5%, preferably <4%, <3%, or <2%, more preferably <1%, <0.5%, or 0% | quercetin, kaempferol, myricetin, fisetin, galangin, isorhamnetin, pachypodol, rhamnazin, pyranoflavonols, furanoflavonols, luteolin, apigenin, tangeritin, taxifolin (or dihydroquercetin), dihydrokaempferol, hesperetin, naringenin, eriodictyol, homoeriodictyol, genistein, daidzein, glycitein |
| Flavanoid glycosides | <5%, preferably <4%, <3%, or <2%, more preferably <1%, <0.5%, or 0% | hesperidin, naringin, rutin, quercitrin, luteolin-glucoside, quercetin-xyloside |
| Anthocyanidins | <5%, preferably <4%, <3%, or <2%, more preferably <1%, <0.5%, or 0% | cyanidin, delphinidin, malvidin, pelargonidin, peonidin, petunidin |
| Tannins | <1%, preferably <0.5%, <0.25%, or 0% | tannic acid |
| Amino acids + total protein | <0.1%, preferably <0.05%, or 0% | alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <1%, preferably <0.5%, <0.25%, or 0% | monoglycerides, diglycerides, triglycerides |
| Monosaccharides, disaccharides, and polysaccharides | <1% | glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, maltotriose, panose |
| Sugar alcohols | <1% | glycerol, sorbitol, mannitol, xylitol, maltitol, lactitol, erythritol, isomalt, inositol |
| Dietary fiber | <0.1%, preferably <0.05% or 0% | acacia (arabic) gum, agar-agar, algin-alginate, arabynoxylan, beta-glucan, beta mannan, carageenan gum, carob or locust bean gum, fenugreek gum, galactomannans, gellan gum, glucomannan or konjac gum, guar gum, |

TABLE 2-continued

| Class of compounds | Preferred Content Level (% wt) | % wt of compounds in steviol glycoside solubility enhancer solid (dry) compositions |
|---|---|---|
| | | hemicellulose, inulin, karaya gum, pectin, polydextrose, psyllium husk mucilage, resistant starches, tara gum, tragacanth gum, xanthan gum, cellulose, chitin, and chitosan |
| Steviol glycoside compounds | <55% | stevioside; steviolbioside; rubusoside; 13- and 19-SMG; dulcosides A, B, C, D; and rebaudiosides A, B, C, D, E, F, I, M, N, O, T |
| Saponins | <2%, preferably <1%, <0.5%, <0.25%, or 0% | glycosylated ursolic acid and glycosylated oleanolic acid |
| Terpenes other than saponins and steviol glycoside compounds | <2%, preferably <1%, <0.5%, <0.25%, or 0% | eugenol, geraniol, geranial, alpha-ionone, beta-ionone, epoxy-ionone, limonene, linalool, linalool oxide, nerol, damascenone |
| Lipid oxidation products | <2%, preferably <1%, <0.5%, <0.25%, or 0% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.1%, preferably <0.05% or 0% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd)pyrene, Naphthalene, Phenanthrene, Pyrene |
| Other compounds | <0.1%, preferably <0.05% or 0% | chlorophyll, furans, furan-containing chemicals, theobromine, theophylline, and trigonelline |
| | <1%, preferably <0.5%, <0.25%, or 0% | saponins |

Preferably, such a solid (dry) steviol glycoside solubility enhancer includes <50% (wt), e.g., <40% (wt), <30% (wt), or <25% (wt), more preferably <20% (wt), <15% (wt), <10% (wt), <5% (wt), <4% (wt), <3% (wt), <2% (wt), <1% (wt), <0.5% (wt), <0.25% (wt), <0.10% (wt) or 0% (wt), steviol glycoside compounds. In select implementations, such a solid (dry) composition having steviol glycoside solubility enhancer is substantially free of steviol glycoside compounds. Particularly where the steviol glycoside solubility enhancer is derived from *stevia*, e.g., *stevia* leaves, reducing the amount of steviol glycoside compounds in the steviol glycoside solubility enhancer allows more precise selection of the steviol glycoside s to achieve a desired flavor profile in use.

In one aspect, a solid (dry) sweetener composition, which may be a powder, has steviol glycoside and a steviol glycoside solubility enhancer that does not include one or more of the following compounds, or any combination thereof, above the disclosed preferred content levels. All preferred content levels are stated as weight percentage on a dry weight basis. For those compounds listed that are acids, the compound may be present in acid form and/or in salt form.

TABLE 3

| Class of compounds | Preferred Content Level (% wt) | % wt of compounds in solid (dry) sweetener composition |
|---|---|---|
| Organic acids | <3%, preferably <2%, <1%, or 0% | Malonate, malonic acid, Oxalate, oxalic acid, Lactate, lactic acid, Succinate, succinic acid, Malate, malic acid, Citrate, citric acid |
| | <0.5%, preferably <0.25% or 0% | Tartrate, tartaric acid, Pyruvate, pyruvic acid, Fumarate, fumaric acid, Ascorbic acid, Sorbate, sorbic acid, Acetate, acetic acid |
| Inorganic acids | <1%, preferably <0.5% or 0% | Sulfate, sulfuric acid, Phosphate, phosphoric acid, Nitrate, nitric acid, Nitrite, nitrous acid, Chloride, hydrochloric acid, Ammonia, ammonium |
| Flavanoids, isoflavanoids, and neoflavanoids | <5%, preferably <4%, <3%, or <2%, more preferably <1%, <0.5%, or 0% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |
| Flavanoid glycosides | <5%, preferably <4%, <3%, or <2%, more preferably <1%, <0.5%, or 0% | Hesperidin, Naringin, Rutin, Quercitrin, luteolin-glucoside, quercetin-xyloside |
| Anthocyanidins | <5%, preferably <4%, <3%, or <2%, more preferably <1%, <0.5%, or 0% | Cyanidin, Delphinidin, Malvidin, Pelargonidin, Peonidin, Petunidin |

TABLE 3-continued

| Class of compounds | Preferred Content Level (% wt) | % wt of compounds in solid (dry) sweetener composition |
|---|---|---|
| Tannins | <1%, preferably <0.5%, <0.25%, or 0% | Tannic acid |
| Amino acids + total protein | <0.1%, preferably <0.05%, or 0% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <1%, preferably <0.5%, <0.25%, or 0% | Monoglycerides, diglycerides, triglycerides |
| Monosaccharides, disaccharides, and polysaccharides | <1% | Glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, and maltotriose, panose |
| Sugar alcohols | <1% | Glycerol, Sorbitol, mannitol, xylitol, maltitol, lactitol, erythritol, isomalt, inositol |
| Dietary fiber | <0.1%, preferably <0.05% or 0% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Polydextrose, Psyllium husk mucilage, Resistant starches, Tara gum, Tragacanth gum, Xanthan gum, Cellulose, Chitin, and Chitosan |
| Steviol glycoside compounds | <75% | Stevioside; steviolbioside; rubusoside; 13- and 19-SMG; Dulcosides A, B, C, D; and rebaudiosides A, B, C, D, E, F, I, M, N, O, T |
| Saponins | <1%, preferably <0.5%, <0.25%, or 0% | glycosylated ursolic acid and glycosylated oleanolic acid |
| Terpenes other than saponins and steviol glycoside compounds | <1%, preferably <0.5%, <0.25%, or 0% | eugenol, geraniol, geranial, alpha-ionone, beta-ionone, epoxy-ionone, limonene, linalool, linalool oxide, nerol, damascenone |
| Lipid oxidation products | <1%, preferably <0.5%, <0.25%, or 0% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.05%, preferably <0.01% or 0% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd)pyrene, Naphthalene, Phenanthrene, Pyrene |
| Other compounds | <0.1%, preferably <0.05% or 0% | chlorophyll, furans, furan-containing chemicals, theobromine, theophylline, and trigonelline |

In one aspect, a liquid sweetener concentrate has steviol glycoside and a steviol glycoside solubility enhancer that does not include one or more of the following compounds, or any combination thereof, above the disclosed preferred content levels. These preferred content levels are stated as weight percentage of the liquid sweetener concentrate. For those compounds listed that are acids, the compound may be present in acid form and/or in salt form, taking into account either may be dissociated in the liquid sweetener concentrate.

TABLE 4

| Class of compounds | Preferred Content Level (% wt) | % (wt) of compounds in liquid mixtures of steviol glycoside and steviol algcoside solubility enhancer |
|---|---|---|
| Organic acids | <0.3%, preferably <0.2%, <0.1%, or 0% | Malonate, malonic acid, Oxalate, oxalic acid, Lactate, lactic acid, Succinate, succinic acid, Malate, malic acid |
| | <0.05%, preferably <0.025% or 0% | Tartrate, tartaric acid, Pyruvate, pyruvic acid, Fumarate, fumaric acid, Ascorbic acid, Sorbate, sorbic acid, Acetate, acetic acid |
| Inorganic acids | <1%, preferably <0.05% or 0% | Sulfate, sulfuric acid, Nitrate, nitric acid, Nitrite, nitrous acid, Chloride, hydrochloric acid, Ammonia, ammonium |
| Flavanoids, isoflavanoids, and neoflavanoids | <0.5%, preferably <0.4%, <0.3%, or <0.2%, more preferably <0.1%, <0.05%, or 0% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |

TABLE 4-continued

| Class of compounds | Preferred Content Level (% wt) | % (wt) of compounds in liquid mixtures of steviol glycoside and steviol algcoside solubility enhancer |
|---|---|---|
| Flavanoid glycosides | <0.5%, preferably <0.4%, <0.3%, or <0.2%, more preferably <0.1%, <0.05%, or 0% | Hesperidin, Naringin, Rutin, Quercitrin, luteolin-glucoside, quercetin-xyloside |
| Anthocyanidins | <0.5%, preferably <0.4%, <0.3%, or <0.2%, more preferably <0.1%, <0.05%, or 0% | Cyanidin, Delphinidin, Malvidin, Pelargonidin, Peonidin, Petunidin |
| Tannins | <0.1%, preferably <0.05%, <0.025%, or 0% | Tannic acid |
| Amino acids + total protein | <0.01% preferably <0.005%, or 0% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <0.1%, preferably <0.05%, <0.025%, or 0% | Monoglycerides, diglycerides, triglycerides |
| Monosaccharides, disaccharides, and polysaccharides | <0.1% | Glucose, fructose, sucrose, galactose, ribose, trehalose, trehalulose, lactose, maltose, isomaltose, isomaltulose, mannose, tagatose, arabinose, rhamnose, xylose, dextrose, erythrose, threose, and maltotriose, panose |
| Sugar alcohols | <0.1% | Glycerol, Sorbitol, mannitol, xylitol, maltitol, lactitol, erythritol, isomalt, inositol |
| Dietary fiber | <0.01%, preferably <0.005% or 0% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Polydextrose, Psyllium husk mucilage, Resistant starches, Tara gum, Tragacanth gum, Xanthan gum, Cellulose, Chitin, and Chitosan |
| Saponins | <0.5%, preferably <0.4%, <0.3%, or <0.2%, more preferably <0.1%, <0.05%, or 0% | glycosylated ursolic acid and glycosylated oleanolic acid |
| Terpenes other than steviol glycoside compounds and saponins <0.05%, or 0% | <0.5%, preferably <0.4%, <0.3%, or <0.2%, more preferably <0.1%, | eugenol, geraniol, geranial, alpha-ionone, beta-ionone, epoxy-ionone, limonene, linalool, linalool oxide, nerol, damascenone |
| Lipid oxidation products | <0.5%, preferably <0.4%, <0.3%, or <0.2%, more preferably <0.1%, <0.05%, or 0% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.01% (100 ppm), preferably <0.005% (50 ppm), or 0% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd)pyrene, Naphthalene, Phenanthrene, Pyrene |
| Other compounds | <0.05%, preferably <0.01% or 0% | chlorophyll, furans, furan-containing chemicals, theobromine, theophylline, and trigonelline |

In one aspect, a beverage having steviol glycoside and steviol glycoside solubility enhancer does not include one or more of the following compounds, or any combination thereof, at the disclosed wt % cutoffs. All preferred content levels are stated as weight percentage of the total liquid sweetener concentrate. For those compounds listed that are acids, the compound may be present in acid form and/or in salt form, taking into account that either may be dissociated in the beverage.

TABLE 5

| Class of compounds | Preferred Content Level (% wt) | % (wt) of compounds in beverages having steviol glycoside and steviol glycoside solubility enhancer |
|---|---|---|
| Organic acids | <0.1%, preferably <0.05%, <0.025%, or 0% | Malonate, malonic acid, Oxalate, oxalic acid, Pyruvate, pyruvic acid, Fumarate, fumaric acid |
| Inorganic acids | <1%, preferably <0.05% or 0% | Sulfate, sulfuric acid, Nitrate, nitric acid, Nitrite, nitrous acid, Ammonia, ammonium |
| Flavanoids, isoflavanoids, and neoflavanoids | <0.5%, preferably <0.4%, <0.3%, or <0.2%, more preferably <0.1%, <0.05%, or 0% | Quercetin, Kaempferol, Myricetin, Fisetin, Galangin, Isorhamnetin, Pachypodol, Rhamnazin, Pyranoflavonols, Furanoflavonols, Luteolin, Apigenin, Tangeritin, Taxifolin (or Dihydroquercetin), Dihydrokaempferol, Hesperetin, Naringenin, Eriodictyol, Homoeriodictyol, Genistein, Daidzein, Glycitein |
| Flavanoid | <0.5%, preferably <0.4%, <0.3%, or <0.2%, more preferably <0.1%, <0.05%, or 0% | Hesperidin, Naringin, Rutin, Quercitrin, luteolin-glucoside, quercetin-xyloside glycosides |
| Anthocyanidins | <0.5%, preferably <0.4%, <0.3%, or <0.2%, more preferably <0.1%, <0.05%, or 0% | Cyanidin, Delphinidin, Malvidin, Pelargonidin, Peonidin, Petunidin |
| Tannins | <0.1%, preferably <0.05%, <0.025%, or 0% | Tannic acid |
| Amino acids + total protein | <5%, preferably <1%, <0.5%, <0.1% <0.05%, or 0% | Alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine |
| Total Fat | <0.5%, preferably <0.1%, <0.05%, <0.025%, or 0% | Monoglycerides, diglycerides, triglycerides |
| Dietary fiber | <5%, preferably <1%, <0.5%, <0.1% <0.05%, or 0% | Acacia (arabic) gum, Agar-agar, Algin-alginate, Arabynoxylan, Beta-glucan, Beta mannan, Carageenan gum, Carob or locust bean gum, Fenugreek gum, Galactomannans, Gellan gum, Glucomannan or konjac gum, Guar gum, Hemicellulose, Inulin, Karaya gum, Pectin, Polydextrose, Psyllium husk mucilage, Resistant starches, Tara gum, Tragacanth gum, Xanthan gum, Cellulose, Chitin, and Chitosan |
| Saponins | <0.1%, preferably <0.05%, <0.025%, or 0% | glycosylated ursolic acid and glycosylated oleanolic acid |
| Terpenes other than saponins and steviol glycoside compounds | <0.1%, preferably <0.05%, <0.025%, or 0% | eugenol, geraniol, geranial, alpha-ionone, beta-ionone, epoxy-ionone, limonene, linalool, linalool oxide, nerol, damascenone |
| Lipid oxidation products | <0.1%, preferably <0.05%, <0.025%, or 0% | Decanone, decenal, nonenal, octenal, heptenal, hexenal, pentenal, pentenol, pentenone, hexenone, hydroxynonenal, malondialdehyde |
| Polycyclic Aromatic Hydrocarbons | <0.001% (10 ppm), preferably <0.0005% (5 ppm), or 0% | Acenaphthene, Acenaphthylene, Anthracene, Benzo(a)anthracene, Benzo(a)pyrene, Benzo(b)fluoranthene, Benzo(ghi)perylene, Benzo(k)fluoranthene, Chrysene, Dibenzo(a,h)anthracene, Fluoranthene, Fluorene, Indeno(1,2,3-cd)pyrene, Naphthalene, Phenanthrene, Pyrene |
| Other compounds | <0.05%, preferably <0.01% or 0% | chlorophyll, furans, furan-containing chemicals, theobromine, theophylline, and trigonelline |

Solubility Enhancers

Examples of solubility enhancer include:

caffeic acid; an ester of caffeic acid; an ester of caffeic acid and quinic acid; a monocaffeoylquinic acid, namely an ester of caffeic acid and quinic acid comprising a single caffeic acid moiety, e.g., chlorogenic, cryptochlorogenic, or neochlorogenic acid (structures of each are provided herein); an ester of caffeic acid and quinic acid comprising more than one caffeic acid moiety, such as a dicaffeoylquinic acid, namely an ester of caffeic acid and quinic acid comprising two caffeic acid moieties, e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, or 4,5-dicaffeoylquinic acid (structures of each are provided herein);

ferulic acid; an ester of ferulic acid; an ester of ferulic acid and quinic acid; a monoferuloylquinic acid, namely an ester of ferulic acid and quinic acid comprising a single ferulic acid moiety, e.g., 3-O-feruloylquinic acid, 4-O-feruloylquinic acid, 5-O-feruloylquinic acid; an ester of ferulic acid and quinic acid comprising more than one ferulic acid moiety, such as a diferuloylquinic acid, namely an ester of ferulic acid and quinic acid comprising two ferulic acid moieties, e.g., 1,3-diferuloylquinic acid, 1,4-diferuloylquinic acid, 1,5-diferuloylquinic acid, 3,4-diferuloylquinic acid, 3,5-diferuloylquinic acid, and 4,5-diferuloylquinic acid;

quinic acid, an ester of quinic acid;

tartaric acid, a tartaric acid derivative, an ester of tartaric acid, an ester of a tartaric acid derivative;

3-(3,4-dihydroxyphenyl)lactic acid, a 3-(3,4-dihydroxyphenyl)lactic acid derivative, an ester of 3-(3,4-dihydroxyphenyl)lactic acid, an ester of a 3-(3,4-dihydroxyphenyl)lactic acid derivative;

p-coumaric acid, an ester of p-coumaric acid, an ester of p-coumaric acid and quinic acid, an ester of p-coumaric acid and quinic acid comprising a single p-coumaric acid moiety, an ester of p-coumaric acid and quinic acid comprising more than one p-coumaric acid moiety; and sinapic acid, an ester of sinapic acid, an ester of sinapic acid and quinic acid, an ester of sinapic acid and quinic acid comprising a single sinapic acid moiety, an ester of sinapic acid and quinic acid comprising more than one sinapic acid moiety.

The steviol glycoside solubility enhancer may be in its acid form or in a salt form, e.g., as a quaternary ammonium, sodium, potassium, lithium, magnesium, or calcium salt or combination of such salts. In an aqueous solution, the steviol glycoside solubility enhancer may be dissociated or undissociated, e.g., part or all of a potassium salt of an acid steviol glycoside solubility enhancer compound may be dissociated into a potassium cation and an anion.

In some aspects, the solubility enhancer compound comprises one or more compounds selected from the group consisting of 3-O-coumaroylquinic acid, 4-O-coumaroylquinic acid, 5-O-coumaroylquinic acid, 1,3-dicoumaroylquinic acid, 1,4-dicoumaroylquinic acid, 1,5-dicoumaroylquinic acid, 3,4-dicoumaroylquinic acid, 3,5-dicoumaroylquinic acid, 4,5-dicoumaroylquinic acid.

Caffeic acid has the structure:

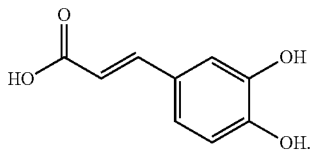 [SMILES: O=C(O)/C=C/c1ccc(O)c(O)c1]

Ferulic acid has the structure:

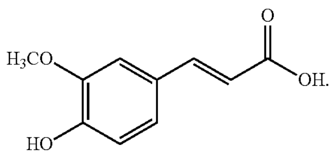 [SMILES: COc1cc(/C=C/C(=O)O)ccc1O]

p-Coumaric acid has the structure:

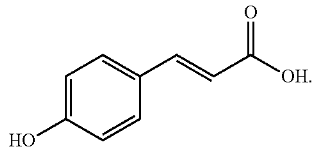 [SMILES: O=C(O)/C=C/c1ccc(O)cc1]

Sinapic acid has the structure:

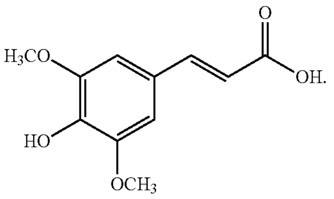 [SMILES: COc1cc(/C=C/C(=O)O)cc(OC)c1O]

Quinic acid has the structure:

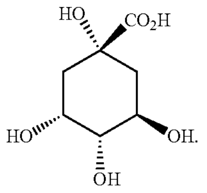 [SMILES: O=C(O)[C@]1(O)C[C@@H](O)[C@@H](O)[C@H](O)C1]

3-(3,4-dihydroxyphenyl)lactic acid has the structure:

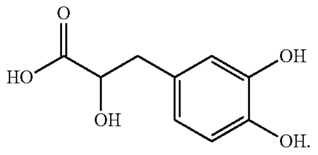 [SMILES: O=C(O)C(O)Cc1ccc(O)c(O)c1]

Tartaric acid has the structure:

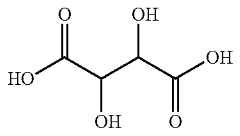

and can be in the D and L forms.

Examples of the esters of the various acids contemplated herein include the ester of caffeic acid and tartaric acid, which includes cichoric acid having the structure:

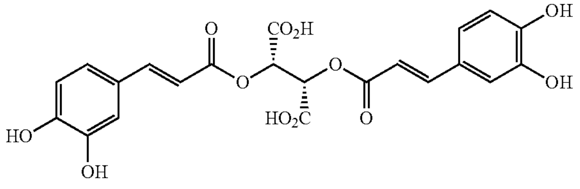 [SMILES: O=C(/C=C/c1ccc(O)c(O)c1)O[C@H](C(=O)O)[C@H](OC(=O)/C=C/c1ccc(O)c(O)c1)C(=O)O]

which has two caffeic acid molecules linked to a tartaric acid core; and caftaric acid having the structure:

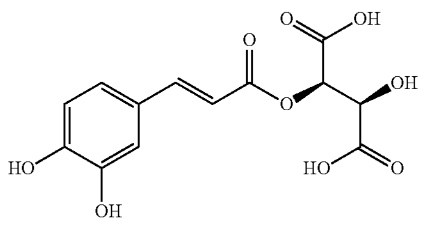 [SMILES: O=C(/C=C/c1ccc(O)c(O)c1)O[C@@H](C(=O)O)[C@@H](O)C(=O)O]

which has one caffeic acid molecule linked to a tartaric acid core.

Examples of the esters of the various acids contemplated herein also include the ester of caffeic acid and 3-(3,4-dihydroxyphenyl)lactic acid including, for example, rosmarinic acid, which has the structure:

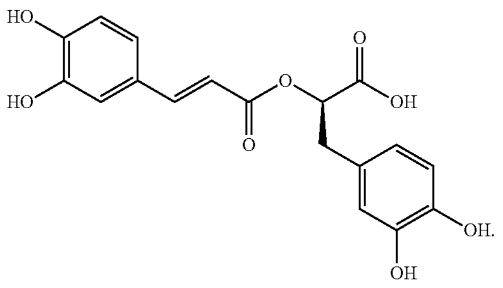 [SMILES: O=C(/C=C/c1ccc(O)c(O)c1)O[C@H](Cc1ccc(O)c(O)c1)C(=O)O]

Examples of the esters of the various acids contemplated herein include the ester of caffeic acid and quinic acid, which includes monocaffeoylquinic acids (e.g., chlorogenic acid, neochlorogenic acid, and cryptochlorogenic acid), and dicaffeoylquinic acids (e.g., 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, and 4,5-dicaffeoylquinic acid), and salts thereof:

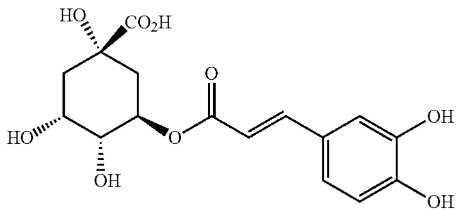

Chlorogenic acid

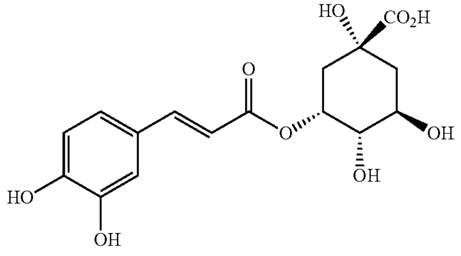

Neochlorogenic acid

-continued

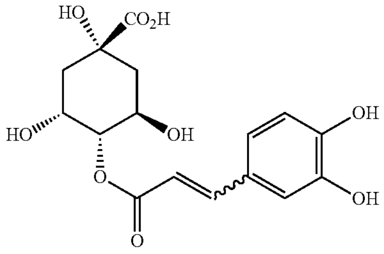

Cryptochlorogenic acid

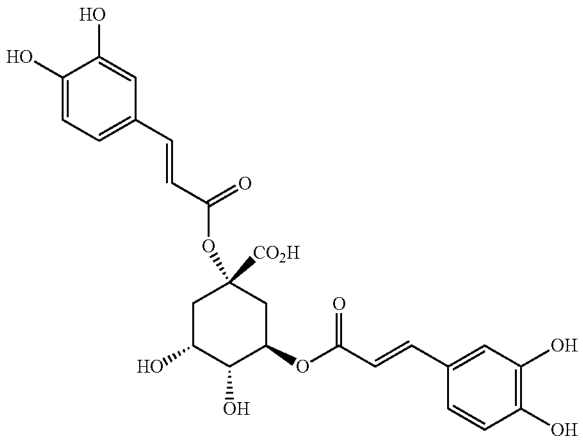

1,5-Dicaffeoylquinic acid

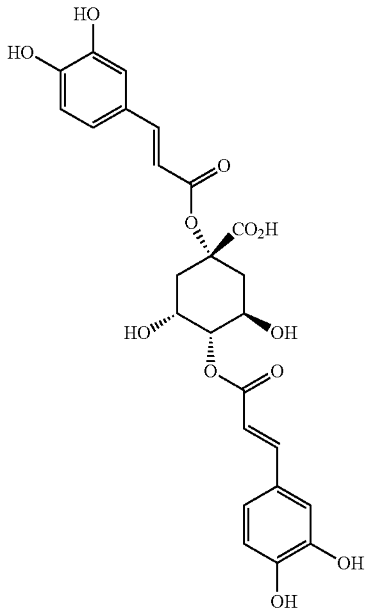

1,4-Dicaffeoylquinic acid

-continued

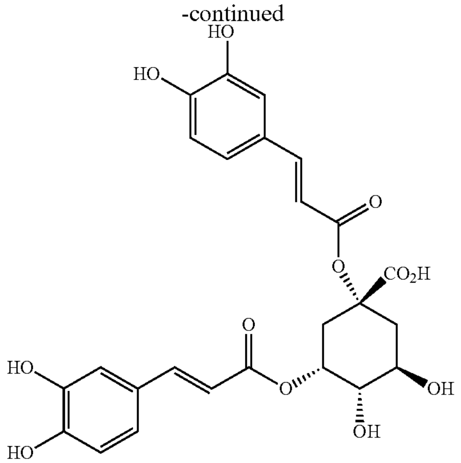

1,3-Dicaffeoylquinic acid

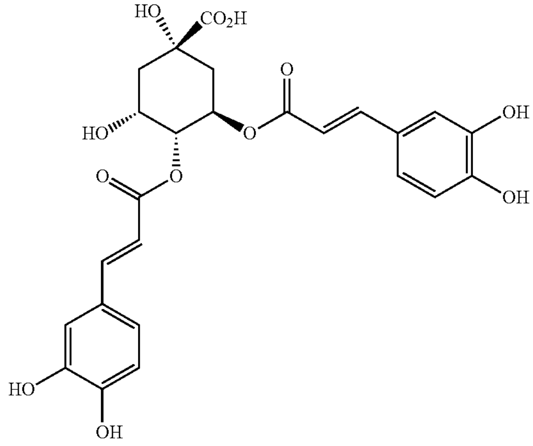

4,5-Dicaffeoylquinic acid

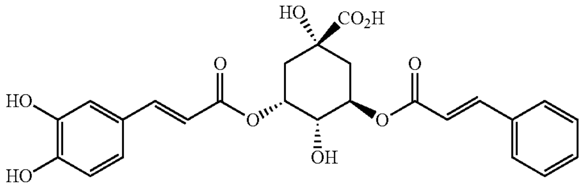

3,5-Dicaffeoylquinic acid

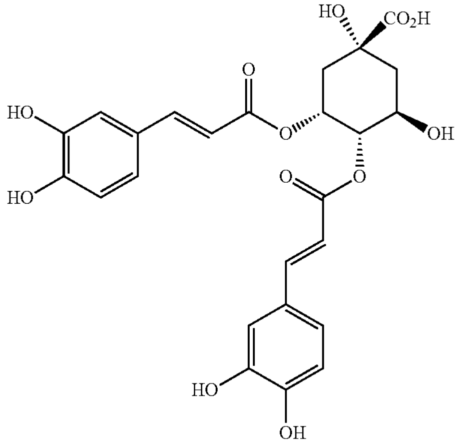

3,4-Dicaffeoylquinic acid with 4,5-dicaffeoylquinic acid, 3,5-dicaffeoylquinic acid, and 3,4-dicaffeoylquinic acid being most prevalent in the compositions contemplated herein and most prevalent in abundance in *stevia*, yerba mate, globe artichoke, and green coffee.

Each of the caffeic acid, monocaffeoylquinic acids, dicaffeoylquinic acids and other solubility enhancer compounds can be considered weak acids and can each exist in at least one of their conjugate acid form, conjugate base form (e.g., in their salt form), and mixed conjugate acid-conjugate base form, wherein a fraction (e.g., mole fraction) of the compounds exist in the conjugate acid form and another fraction exist in the conjugate base form. The fraction of conjugate acid form to conjugate base form for the caffeic acid, monocaffeoylquinic acids, dicaffeoylquinic acids, and other solubility enhancer compounds will depend on various factors, including the pKa of each compound and the pH of the composition.

Examples of salts of caffeic acid, monocaffeoylquinic acids, dicaffeoylquinic acids, and other steviol glycoside solubility enhancer compounds include, but are not limited to, their quaternary ammonium, sodium, potassium, lithium, magnesium, and calcium salts or combination of such salts.

In some aspects, the solubility enhancer can be enriched for one or more of caffeic acid, monocaffeoylquinic acids, and dicaffeoylquinic acids. The term "enriched" refers to an increase in an amount of one of caffeic acid, monocaffeoylquinic acids, and dicaffeoylquinic acids relative to one or more other compounds that are present in the solubility enhancer. A solubility enhancer that is enriched for one or more of caffeic acid, monocaffeoylquinic acids, and dicaffeoylquinic acids can increase solubility of the steviol glycoside composition.

In some aspects, a solubility enhancer enriched for one or more dicaffeoylquinic acids can increase solubility of the steviol glycoside composition. A solubility enhancer that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more dicaffeoylquinic acids. In other aspects, a solubility enhancer that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

In some aspects, an amount of solubility enhancer effective to increase solubility of the steviol glycoside includes one or more dicaffeoylquinic acids and comprising 10% or more, 15% or more, 20% or more, 25% or more, 30% or more, 35% or more, 40% or more, 45% or more, or 50% or more, 60% or more, 70% or more, or 80% or more, or 90% or more dicaffeoylquinic acids. In other aspects, a solubility enhancer that is enriched for dicaffeoylquinic acids can comprise 10% or more, 15% or more, 20% or more, 25% or more, 30% or more, 35% or more, 40% or more, 45% or more, or 50% or more, 60% or more, 70% or more, or 80% or more, or 90% or more of a combination of one or more of 1,3-dicaffeoylquinic acid, 1,4-dicaffeoylquinic acid, 1,5-dicaffeoylquinic acid, 3,4-dicaffeoylquinic, 3,5-dicaffeoylquinic acid, and 4,5-dicaffeoylquinic acid, and salts thereof.

Mono- and Dicaffeoylquinic Components

Certain preferred steviol glycoside solubility enhancers specifically include a dicaffeoylquinic (DCQ) component and, optionally, a monocaffeoylquinic (MCQ) component. The DCQ component includes at least one, desirably at least 2 or at least 3, dicaffeoylquinic acids or salts thereof. In one aspect, the DCQ component includes at least one compound selected from the group consisting of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof. The MCQ component includes at least one, desirably at least 2 or at least 3, monocaffeoylquinic acids or salts thereof. In one aspect, the MCQ component includes at least one compound selected from the group consisting of chlorogenic acid, cryptochlorogenic acid, neochlorogenic acid, and salts thereof.

The DCQ component and the MCQ component (if present) may together comprise more than 50% (wt) of the steviol glycoside solubility enhancer. Desirably, the DCQ component and the MCQ component (if present) together comprise more than 60% (wt), more than 70% (wt), more than 80% (wt), more than 90% (wt), more than 95% (wt), or more than 98% (wt) of the steviol glycoside solubility enhancer.

The steviol glycoside solubility enhancer may include solubility enhancer compounds in addition to the MCQ and DCQ components. One useful steviol glycoside solubility enhancer includes the MCQ component, the DCQ component, and one or more compounds selected from the group consisting of caffeic acid, ferulic acid, p-coumaric acid, sinapic acid, quinic acid, 3-(3,4-dihydroxyphenyl)lactic acid, tartaric acid, chicoric acid, caftaric acid, monoferuloylquinic acids, diferuloylquinic acids, monocoumaroylquinic acids, dicoumaroylquinic acids, and salts thereof. In certain aspects, such a steviol glycoside solubility enhancer includes the MCQ component, the DCQ component, and one or more compounds selected from the group consisting of caffeic acid, monoferuloylquinic acids, diferuloylquinic acids, and salts thereof.

One useful steviol glycoside solubility enhancer includes a MCQ component, a DCQ component, and less than 0.3% (wt) of malonate, malonic acid, oxalate, oxalic acid, lactate, lactic acid, succinate, succinic acid, malate, or malic acid; or less than 0.05% (wt) of pyruvate, pyruvic acid, fumarate, fumaric acid, tartrate, tartaric acid, sorbate, sorbic acid, acetate, or acetic acid; or less than about 0.05% (wt) of chlorophyll. In one aspect, the steviol glycoside solubility enhancer is free of malonate, malonic acid, oxalate, oxalic acid, lactate, lactic acid, succinate, succinic acid, malate, and malic acid; or is free of pyruvate, pyruvic acid, fumarate, fumaric acid, tartrate, tartaric acid, sorbate, sorbic acid, acetate, and acetic acid; or is chlorophyll-free.

Surprisingly, the weight ratio of a DCQ component to a MCQ component can materially impact the effectiveness, on a weight basis, of a steviol glycoside solubility enhancer. In particular, higher weight ratios of the DCQ component to the MCQ component are generally more effective at keeping steviol glycoside compounds in solution. This is particularly surprising given that, all other things being equal, the total number of molecules in a given weight of the steviol glycoside solubility enhancer decreases as that weight ratio increases (since a monocaffeoylquinic acid has a lower molecular weight than a dicaffeoylquinic acid, there are more molecules in a gram of monocaffeoylquinic acid than in a gram of dicaffeoylquinic acid).

A weight ratio of the DCQ component to the MCQ component (i.e., the weight of the DCQ component divided by the weight of the MCQ component) may be at least 0.2, at least 0.33, or at least 0.5. Preferably, this ratio is at least 1, at least 2, at least 3, at least 4, at least 5, at least 6, at least 7, at least 8, at least 9, or at least 10. In certain aspects, this ratio is no more than 20 or no more than 10, e.g., between 1 and 20, preferably between 1 and 10, between 2 and 10, between 3 and 10, between 4 and 10, or between 5 and 10. Depending on the botanical source, getting increasingly higher ratios of the DCQ component to the MCQ component may increase processing cost to obtain the solubility enhancer without adversely impacting a commercially relevant use, e.g., in a beverage having less than 1,000 ppm of steviol glycoside.

Certain commercially useful steviol glycoside solubility enhancers have a weight ratio of the DCQ component to the MCQ component of between 0.33 and 5. Such compositions were found to produce non-alcoholic beverages with particularly desirable sensory properties. Thus, in some aspects the weight ratio of the DCQ component to the MCQ component in the steviol glycoside solubility enhancer is between 0.33 and 5, between 0.5 and 5, between 1 and 5, between 1.5 and 5, between 2 and 5, between 3 and 5, between 0.5 and 4, between 1 and 4, between 1.5 and 4, between 0.5 and 3, between 1 and 3, or between 1.5 and 3.

One suitable steviol glycoside solubility enhancer has a weight ratio of the DCQ component to the MCQ component of at least 1, preferably at least 2, at least 3, or at least 4 and the DCQ component and MCQ component together comprise more than 70% (wt), e.g., more than 80% (wt) or more than 90% (wt), of the steviol glycoside solubility enhancer.

One can gauge effectiveness of a steviol glycoside solubility enhancer by using the following standardized solubility test: The steviol glycoside solubility enhancer and a steviol glycoside including 89% (wt) rebaudioside M and 8.2% (wt) rebaudioside D (based on the weight of the total steviol glycoside content) are added to distilled water. The steviol glycoside solubility enhancer is added at a concentration of 35.7 grams per liter of water (3.57% (wt/vol)) and the steviol glycoside is added at a concentration of 50 grams per liter of water (5% (wt/vol)). The water is then heated to 80° C. for ten minutes with periodic mixing to form a solution. The solution is cooled to 22° C. then stored at 22° C. The solution is then visually inspected periodically for precipitate, indicating that the steviol glycoside is coming out of solution. The storage period, i.e., the time in storage at 22° C., that the steviol glycoside remains in solution is recorded.

Steviol glycoside solubility enhancers in accordance with aspects of the invention may maintain the steviol glycoside in solution for a storage period, measured in accordance with this standardized solubility test, of at least 3 days, at least 5 days, or at least 6 days. This storage period is desirably at least 7 days, at least 10 days, at least 14 days, at least 21 days, or at least 28 days. Particularly commercially useful steviol glycoside solubility enhancers may maintain the steviol glycoside in solution for a storage period of at least 6 weeks, at least 8 weeks, or at least 12 weeks. This may enable a beverage throw syrup or a "water-enhancing" beverage concentrate with commercially relevant shelf life even if it is free of C1-C4 alcohols.

Ratio of Steviol Glycoside to Steviol Glycoside Solubility Enhancer

In some aspects, an amount of steviol glycoside solubility enhancer effective to increase solubility of the steviol glycoside is an amount such that the solubility enhancer comprises a 1:0.3 to 1:3 ratio by weight of steviol glycoside to solubility enhancer. In other aspects, an amount of solubility enhancer effective to increase solubility of the steviol glycoside is an amount such that the solubility enhancer comprises a 1:1 to 1:3 ratio by weight of steviol glycoside to solubility enhancer. An amount of solubility enhancer effective to increase solubility of the steviol glycoside can be an amount such that the solubility enhancer comprises a ratio by weight of steviol glycoside to solubility enhancer of 1:0.1 to 1:10. In some aspects an amount of solubility enhancer effective to increase solubility of the steviol glycoside can be an amount such that the solubility enhancer comprises a ratio by weight of steviol glycoside to solubility enhancer of about 1:0.1 to 1:5, about 1:0.5 to 1:4, about 1:0.3 to 1:3, or about 1:1 to 1:3. In other aspects an amount of solubility enhancer effective to increase solubility of the steviol glycoside can be an amount such that the solubility enhancer comprises a ratio by weight of steviol glycoside to solubility enhancer of about 1:0.1, 1:0.5, 1:1, 1:2, 1:3, 1:4, 1:5, 1:6, 1:7, 1:8, 1:9, or 1:10 by weight. In some aspects, an amount of solubility enhancer effective to increase solubility of the steviol glycoside can be an amount such that the solubility enhancer comprises a ratio by weight of steviol glycoside to solubility enhancer of about 1:0.3 to 1:3.

In some aspects, an amount of solubility enhancer effective to increase solubility of the steviol glycoside is a final concentration of solubility enhancer of greater than 100 ppm, 200 ppm, 300 ppm, 400 ppm, 700 ppm, 800 ppm, 900 ppm, or 1000 ppm. The final concentration of solubility enhancer can be greater than 1100 ppm, 1200 ppm, 1300 ppm, 1400 ppm, 1500 ppm, 1600 ppm, 1700 ppm, 1800 ppm, or 1900 ppm. The final concentration of solubility enhancer can be greater than 2100 ppm, 2200 ppm, 2300 ppm, 2400 ppm, 2500 ppm, 2600 ppm, 2700 ppm, 2800 ppm, or 2900 ppm. The final concentration of solubility enhancer can be greater than 3100 ppm, 3200 ppm, 3300 ppm, 3400 ppm, 3500 ppm, 3600 ppm, 3700 ppm, 3800 ppm, or 3900 ppm. The final concentration of solubility enhancer can be greater than 3000 ppm, 4000 ppm, 5000 ppm, 6000 ppm, 7000 ppm, 8000 ppm, or 9000 ppm. The final concentration of solubility enhancer can be greater than 1%, 2%, 3%, 4%, 5%, 6%, 7%, 8%, 9%, 10%, or higher.

In some aspects, the steviol glycoside composition comprises an increased solubility when dissolved in a primarily aqueous solution that comprises primarily water. The primarily aqueous solution can also comprise less than less than 45%, 40%, 30%, 20%, 15%, 10%, 5%, or 1% of C1-C4 alcohol by weight. In one commercially relevant The primarily aqueous solution can be substantially free (below 0.2% (wt)) of C1-C4 alcohols, e.g., a non-alcoholic beverage. In other aspects, the primarily aqueous solution is essentially free (below 0.05% (wt)) of C1-C4 alcohols. In some aspects, the primarily aqueous solution comprises less than 1% stevioside. The primarily aqueous solution can comprise less than 3% rebaudioside B. The primarily aqueous solution can comprise less than 1% steviolbioside. The primarily aqueous solution can comprise less than 1% 13-SMG. In other aspects, the primarily aqueous solution comprises less than one or more of 1% stevioside, 1% rebaudioside B, 1% steviolbioside, and 1% 13-SMG.

The primarily aqueous solution may have any suitable pH, e.g., between 0 and 7, between 1 and 6, or between 1.5 and 4.

Beverages may be made with steviol glycoside solubility enhancer and steviol glycoside. Because the steviol glycoside solubility enhancer permits more steviol glycoside to enter solution, such beverages may be zero-calorie beverages sweetened only with steviol glycoside at sweetness levels higher than would otherwise be possible.

EXAMPLES

The following example is provided to illustrate the disclosure, but is not intended to limit the scope thereof. All parts and percentages are by weight unless otherwise indicated.

Example 1

A variety of steviol glycoside solubility enhancer compounds are found in *stevia* leaves and other plant parts, e.g., in the stems of artichokes, and may be in other leaves (tea leaves, etc.) or plant parts. In one embodiment, the solubility enhancer compounds are mono-, di- or tri-hydroxycinnamic acid esters of quinic acid, such as chlorogenic acid, cynarin, neochlorogenic acid, cryptochlorogenic acid, 3-5-dicaffeoylquinic acid, etc. Exemplary methods to purify those solubility enhancers is described below.

Purification from *Stevia* Leaf:

Chlorogenic acid, neochlorogenic acid, cryptochlorogenic acid, cynarin, and other cynarin isomers account for approximately 7% of the material in the *stevia* leaf on a dry weight basis.

Salt Form Steviol Glycoside Solubility Enhancer Compounds:

*Stevia* leaf can be first extracted with 50% (vol/vol) ethanol to liberate all the steviol glycosides and steviol glycoside solubility enhancers from the solids. Once extracted and the solids removed (e.g., via filtration and/or centrifugation), the resulting extract may be acidified to a pH 2-2.5 with a common inorganic acid, such as hydrochloric acid or phosphoric acid. The acidified extract may then be extracted via a liquid-liquid extraction with ethyl acetate to yield purified fractions, and the steviol glycoside compounds (aqueous layer) separated from the steviol glycoside solubility enhancer compounds (organic layer). Each phase can then be further purified separately to obtain the desired final product.

The ethyl acetate layer with the steviol glycoside solubility enhancer compounds may be further purified by adding basic solutions in water (for example, 0.05% calcium hydroxide, 0.1% sodium bicarbonate, etc.) and performing another liquid-liquid extraction. The colored species stay in the ethyl acetate phase and can be discarded, while the aqueous phase contains the solubility enhancer compounds and can be dried directly.

Acid Form Steviol Glycoside Solubility Enhancer Compounds:

*Stevia* leaf may be first extracted with 50% (vol/vol) ethanol to liberate all the steviol glycoside compounds and steviol glycoside solubility enhancer compounds from the solids. Once extracted and the solids removed (e.g., via filtration and/or centrifugation), the resulting extract may be extracted via a liquid-liquid extraction with ethyl acetate to remove colored species. The organic phase can be discarded and the aqueous layer may be acidified to a pH 2-2.5 with a common inorganic acid, such as hydrochloric acid or phosphoric acid. Fresh ethyl acetate may be added and another liquid-liquid extraction may be performed to yield purified fractions, separating the steviol glycosides (aqueous layer) from the steviol glycoside solubility enhancer compounds (organic layer). The aqueous phase, containing steviol glycoside compounds, may be further purified for a desired steviol glycoside-based product, while the organic phase may be dried directly to make the desired steviol glycoside solubility enhancer product in an acid form.

Resin Purification:

Resins, such as polystyrene divinylbenzene and polymethacrylate, may be used to purify these compounds. When using these resins, pH control allows for chlorogenic acid and cynarin isomer purification.

For polymethacrylate resin under acidic conditions, chlorogenic acid elutes before steviol glycoside compounds, while cynarin isomers elute after steviol glycoside compounds using ethanol/water elution. Under neutral conditions, both cynarin isomers and chlorogenic acid elute before steviol glycoside compounds.

For polystyrene divinylbenzene under acidic conditions, chlorogenic acid elutes before steviol glycoside compounds, while cynarin isomers elute with steviol glycoside compounds using ethanol/water elution. Under neutral conditions, both cynarin isomers and chlorogenic acid elute before steviol glycoside compounds.

Other hydrophobic resins and stationary phases can be used to purify these compounds.

Cynarin (and its Isomers) Only Purification:

To purify only cynarin and its isomers (removing chlorogenic acid and its isomers), an aqueous solution of SE material can be made at a high concentration to start the purification. Higher concentrations of cynarin include some base, such as NaOH, usually at ½ molar concentration, resulting in a solution of pH about 4. This material may be loaded on a polymethacrylate resin and washed with water (to remove excess acids). The chlorogenic acid (and its isomers) can be eluted with 15% (vol/vol) ethanol and dried separately to create one product. The column may then be treated with 60% (vol/vol) ethanol to elute cynarin and its isomers. This material can then be dried, e.g., in the absence of strong acids or high heat, to create a cynarin only SE material.

Example 2. Long Term Solubility Tests of Steviol Glycoside Solubility Enhancers with Steviol Glycosides Samples were prepared via the design shown in Table 6, in weight to volume percentage. An appropriate amount of steviol glycoside (SG) was weighed into a 10 mL glass vial and diluted with an appropriate volume of pH 4 citrate buffer, e.g., for 0.6% level, 27 mg was diluted into 4.5 mL of buffer. This was repeated for all conditions in Table 1. Samples that were designed for pH 2.5 were then adjusted via phosphoric acid and pH meter to pH 2.5, dropwise. For these samples, the same lot of *stevia* leaf-derived steviol glycoside solubility enhancer (SE) was used. Two different steviol glycosides were used, RM80 (>80% Reb M on a dry weight basis) and RA95 (>95% Reb A on a dry weight basis).

At each time point, the solutions were centrifuged at 10,000 rpm for two minutes to remove any insoluble material from the analysis (even though none was visible). An aliquot of the supernatant was diluted into 55% methanol for analysis by UHPLC-UV. The chromatographic analysis was performed on a C18-based reversed-phase chromatography column at elevated temperature under gradient conditions, utilizing trifluoroacetic acid in water and acetonitrile. SG was detected utilizing a UV detector set to 210 nm. A linear calibration curve was applied using a high-purity (>99%) Reb A standard as a reference solution.

TABLE 6

| SG % | SG Type | SE % | Storage Cond | pH | Times (weeks) | # of Pulls | # of Replicates |
|---|---|---|---|---|---|---|---|
| 0.6% | RM80 | 0.6% | RT | 2.5 | 0, 14, 26, 52 | 4 | 3 |
| 1.5% | RM80 | 1.5% | RT | 2.5 | 0, 4, 14, 26, 39, 52 | 6 | 1 |
| 3.0% | RM80 | 3.0% | RT | 2.5 | 0, 4, 14, 26, 39, 52 | 6 | 3 |
| 3.0% | RM80 | 4.5% | RT | 2.5 | 0, 4, 14, 26, 39, 52 | 6 | 3 |
| 6.0% | RM80 | 6.0% | RT | 2.5 | 0, 4, 14, 26, 39, 52 | 6 | 1 |
| 6.0% | RA95 | 6.0% | RT | 2.5 | 0, 4, 14, 26, 39, 52 | 6 | 3 |
| 0.6% | RM80 | 0.6% | 4C | 2.5 | 14, 26, 52 | 3 | 1 |
| 1.5% | RM80 | 1.5% | 4C | 2.5 | 4, 14, 26, 39, 52 | 5 | 3 |
| 3.0% | RM80 | 3.0% | 4C | 2.5 | 4, 14, 26, 39, 52 | 5 | 1 |
| 3.0% | RM80 | 4.5% | 4C | 2.5 | 4, 14, 26, 39, 52 | 5 | 1 |
| 6.0% | RM80 | 6.0% | 4C | 2.5 | 4, 14, 26, 39, 52 | 5 | 3 |
| 6.0% | RA95 | 6.0% | 4C | 2.5 | 4, 14, 26, 39, 52 | 5 | 1 |
| 0.6% | RM80 | 0.6% | RT | 4.0 | 0, 14, 26, 52 | 4 | 3 |
| 1.5% | RM80 | 1.5% | RT | 4.0 | 0, 4, 14, 26, 39, 52 | 6 | 1 |
| 3.0% | RM80 | 3.0% | RT | 4.0 | 0, 4, 14, 26, 39, 52 | 6 | 3 |
| 3.0% | RM80 | 4.5% | RT | 4.0 | 0, 4, 14, 26, 39, 52 | 6 | 3 |
| 6.0% | RM80 | 6.0% | RT | 4.0 | 0, 4, 14, 26, 39, 52 | 6 | 1 |
| 35.0% | RM80 | 35.0% | RT | 4.0 | 0, 26, 40, 52 | 4 | 1 |
| 6.0% | RA95 | 6.0% | RT | 4.0 | 0, 4, 14, 26, 39, 52 | 6 | 3 |
| 0.6% | RM80 | 0.6% | 4C | 4.0 | 14, 26, 52 | 3 | 1 |
| 1.5% | RM80 | 1.5% | 4C | 4.0 | 4, 14, 26, 39, 52 | 5 | 3 |
| 3.0% | RM80 | 3.0% | 4C | 4.0 | 4, 14, 26, 39, 52 | 5 | 1 |
| 3.0% | RM80 | 4.5% | 4C | 4.0 | 4, 14, 26, 39, 52 | 5 | 1 |
| 6.0% | RM80 | 6.0% | 4C | 4.0 | 4, 14, 26, 39, 52 | 5 | 3 |
| 6.0% | RA95 | 6.0% | 4C | 4.0 | 4, 14, 26, 39, 52 | 5 | 1 |

Briefly, this long term storage solubility study showed that SG solutions with SE that were stored at 4° C.; room temperature (~22° C.); at pH 4; and at pH 2.5 demonstrated >94% recovery of the SG after 48+ weeks of storage. The long term solubility data is given in Table 7. A value of NM denotes that no measurement was taken at that time.

TABLE 7

| Experiment | Time (weeks) | 0 | 4 | 14 | 26 | 39 | 40 | 48 |
|---|---|---|---|---|---|---|---|---|
| 6% RA95 with 6% SE at 4C and pH 2.5 | Reb A % Recovery | 100.0 | 99.5 | 98.3 | 98.3 | 98.6 | NM | 98.5 |
| 6% RA95 with 6% SE at 4C and pH 4 | Reb A % Recovery | 100.0 | 98.8 | 99.1 | 98.0 | 98.7 | NM | 98.6 |
| 6% RA95 with 6% SE at RT and pH 2.5 | Reb A % Recovery | 100.0 | 99.5 | 98.6 | 98.2 | 98.0 | NM | 97.8 |
| 6% RA95 with 6% SE at RT and pH 4 | Reb A % Recovery | 100.0 | 99.4 | 98.4 | 98.4 | 98.3 | NM | 98.3 |
| 0.6% RM80 with 0.6% SE at 4C and pH 2.5 | Reb M % Recovery | 100.0 | NM | 102.4 | 102.4 | NM | NM | 98.0 |
| 0.6% RM80 with 0.6% SE at 4C and pH 4 | Reb M % Recovery | 100.0 | NM | 102.8 | 102.6 | NM | NM | 99.0 |
| 0.6% RM80 with 0.6% SE at RT and pH 2.5 | Reb M % Recovery | 100.0 | NM | 101.1 | 100.2 | NM | NM | 96.0 |
| 0.6% RM80 with 0.6% SE at RT and pH 4 | Reb M % Recovery | 100.0 | NM | 101.7 | 101.5 | NM | NM | 99.2 |
| 1.5% RM80 with 1.5% SE at 4C and pH 2.5 | Reb M % Recovery | 100.0 | 102.6 | 102.6 | 102.5 | 98.5 | NM | 97.9 |
| 1.5% RM80 with 1.5% SE at 4C and pH 4 | Reb M % Recovery | 100.0 | 102.7 | 102.5 | 102.9 | 98.8 | NM | 98.7 |
| 1.5% RM80 with 1.5% SE at RT and pH 2.5 | Reb M % Recovery | 100.0 | 101.8 | 100.8 | 98.6 | 97.3 | NM | 95.3 |
| 1.5% RM80 with 1.5% SE at RT and pH 4 | Reb M % Recovery | 100.0 | 102.1 | 101.5 | 101.8 | 99.2 | NM | 98.3 |
| 3% RM80 with 3% SE at 4C and pH 2.5 | Reb M % Recovery | 100.0 | 102.5 | 102.2 | 102.1 | 98.5 | NM | 97.9 |
| 3% RM80 with 3% SE at 4C and pH 4 | Reb M % Recovery | 100.0 | 102.6 | 102.1 | 102.5 | 98.9 | NM | 98.5 |
| 3% RM80 with 3% SE at RT and pH 2.5 | Reb M % Recovery | 100.0 | 101.8 | 101.0 | 99.8 | 95.9 | NM | 95.0 |
| 3% RM80 with 3% SE at RT and pH 4 | Reb M % Recovery | 100.0 | 102.0 | 101.6 | 101.2 | 98.2 | NM | 97.7 |
| 3% RM80 with 4.5% SE at 4C and pH 2.5 | Reb M % Recovery | 100.0 | 103.5 | 103.4 | 103.3 | 98.3 | NM | 96.7 |
| 3% RM80 with 4.5% SE at 4C and pH 4 | Reb M % Recovery | 100.0 | 103.4 | 102.8 | 103.6 | 97.4 | NM | 97.7 |

TABLE 7-continued

| Experiment | Time (weeks) | 0 | 4 | 14 | 26 | 39 | 40 | 48 |
|---|---|---|---|---|---|---|---|---|
| 3% RM80 with 4.5% SE at RT and pH 2.5 | Reb M % Recovery | 100.0 | 102.7 | 101.5 | 100.6 | 96.2 | NM | 94.0 |
| 3% RM80 with 4.5% SE at RT and pH 4 | Reb M % Recovery | 100.0 | 103.4 | 102.3 | 102.2 | 98.0 | NM | 97.7 |
| 6% RM80 with 6% SE at 4C and pH 2.5 | Reb M % Recovery | 100.0 | 102.0 | 102.0 | 101.8 | 97.9 | NM | 97.4 |
| 6% RM80 with 6% SE at 4C and pH 4 | Reb M % Recovery | 100.0 | 102.0 | 101.6 | 102.2 | 98.3 | NM | 97.7 |
| 6% RM80 with 6% SE at RT and pH 2.5 | Reb M % Recovery | 100.0 | 101.6 | 100.7 | 99.5 | 95.0 | NM | 94.1 |
| 6% RM80 with 6% SE at RT and pH 4 | Reb M % Recovery | 100.0 | 101.6 | 101.2 | 100.8 | 97.2 | NM | 96.7 |
| 35% RM80 with 35% SE at RT and pH 4 | Reb M % Recovery | 100.0 | NM | NM | 99.5 | NM | 95.9 | 96.2 |

The long term storage chemical stability data is given in Table 8. The same samples were also assessed for absolute concentration of the dissolved steviol glycoside compounds. The data presented in Table 8 shows the concentration of steviol glycosides at each time point. In some of the vials, there was some evaporation of the solvent during the year-long experiment. Thus, the concentration increased in most samples over time, but no crystals were observed at any time in any sample. A value of NM denotes that no measurement was taken at that time.

TABLE 8

| Experiment | Time (weeks) | 0 | 4 | 14 | 26 | 39 | 40 | 48 |
|---|---|---|---|---|---|---|---|---|
| 6% RA95 with 6% SE at 4C and pH 2.5 | Reb A (g/L) | 5.69 | 8.57 | 5.37 | 6.18 | 7.76 | NM | 8.44 |
| 6% RA95 with 6% SE at 4C and pH 4 | Reb A (g/L) | 5.21 | 5.39 | 5.13 | 5.63 | 6.45 | NM | 7.06 |
| 6% RA95 with 6% SE at RT and pH 2.5 | Reb A (g/L) | 5.69 | 5.35 | 5.63 | 6.99 | 8.44 | NM | 7.87 |
| 6% RA95 with 6% SE at RT and pH 4 | Reb A (g/L) | 5.21 | 5.15 | 5.78 | 6.06 | 7.21 | NM | 7.41 |
| 0.6% RM80 with 0.6% SE at 4C and pH 2.5 | Reb M (g/L) | 0.45 | NM | 0.44 | 0.44 | NM | NM | 0.55 |
| 0.6% RM80 with 0.6% SE at 4C and pH 4 | Reb M (g/L) | 0.45 | NM | 0.48 | 0.55 | NM | NM | 0.53 |
| 0.6% RM80 with 0.6% SE at RT and pH 2.5 | Reb M (g/L) | 0.45 | NM | 0.45 | 0.47 | NM | NM | 0.57 |
| 0.6% RM80 with 0.6% SE at RT and pH 4 | Reb M (g/L) | 0.45 | NM | 0.49 | 0.54 | NM | NM | 0.77 |

TABLE 8-continued

| Experiment | Time (weeks) | 0 | 4 | 14 | 26 | 39 | 40 | 48 |
|---|---|---|---|---|---|---|---|---|
| 1.5% RM80 with 1.5% SE at 4C and pH 2.5 | Reb M (g/L) | 1.09 | 0.99 | 1.07 | 1.06 | 1.26 | NM | 1.19 |
| 1.5% RM80 with 1.5% SE at 4C and pH 4 | Reb M (g/L) | 1.10 | 1.06 | 1.12 | 1.21 | 1.53 | NM | 1.41 |
| 1.5% RM80 with 1.5% SE at RT and pH 2.5 | Reb M (g/L) | 1.09 | 1.01 | 1.05 | NM | 1.28 | NM | 1.33 |
| 1.5% RM80 with 1.5% SE at RT and pH 4 | Reb M (g/L) | 1.10 | 1.08 | 1.17 | 1.43 | 1.69 | NM | 1.81 |
| 3% RM80 with 3% SE at 4C and pH 2.5 | Reb M (g/L) | 2.11 | 1.99 | 2.08 | NM | 2.71 | NM | 2.45 |
| 3% RM80 with 3% SE at 4C and pH 4 | Reb M (g/L) | 2.06 | 1.99 | 2.09 | 2.18 | 2.64 | NM | 2.44 |
| 3% RM80 with 3% SE at RT and pH 2.5 | Reb M (g/L) | 2.11 | 1.97 | 1.90 | 2.17 | 2.59 | NM | 2.67 |
| 3% RM80 with 3% SE at RT and pH 4 | Reb M (g/L) | 2.06 | 1.98 | 2.18 | 2.50 | 2.86 | NM | 2.96 |
| 3% RM80 with 4.5% SE at 4C and pH 2.5 | Reb M (g/L) | 2.05 | 2.74 | 2.01 | 2.11 | 2.71 | NM | 2.47 |
| 3% RM80 with 4.5% SE at 4C and pH 4 | Reb M (g/L) | 1.98 | 1.95 | 2.09 | 2.14 | 2.53 | NM | 2.30 |
| 3% RM80 with 4.5% SE at RT and pH 2.5 | Reb M (g/L) | 2.05 | 1.99 | 2.08 | 2.28 | 2.72 | NM | 2.84 |
| 3% RM80 with 4.5% SE at RT and pH 4 | Reb M (g/L) | 1.98 | 1.98 | 2.08 | 2.40 | 2.79 | NM | 2.90 |
| 6% RM80 with 6% SE at 4C and pH 2.5 | Reb M (g/L) | 4.54 | 3.98 | 4.25 | 4.67 | 5.62 | NM | 5.25 |
| 6% RM80 with 6% SE at 4C and pH 4 | Reb M (g/L) | 3.83 | 3.86 | 3.99 | 4.30 | 5.02 | NM | 4.72 |
| 6% RM80 with 6% SE at RT and pH 2.5 | Reb M (g/L) | 4.54 | 3.85 | 4.35 | 5.05 | 5.46 | NM | 7.29 |
| 6% RM80 with 6% SE at RT and pH 4 | Reb M (g/L) | 3.83 | 3.72 | 3.71 | 4.34 | 5.32 | NM | 5.41 |
| 35% RM80 with 35% SE at RT and pH 4 | Reb M (g/L) | 20.3 | NM | NM | 24.4 | 24.4 | NM | 27.8 |

This example shows that the steviol glycoside solubility enhancers are effective to solubilize steviol glycoside over time. SE are effective to solubilize steviol glycoside solutions over 48 weeks at 4° C., at room temperature, at pH 4, and/or at pH 2.5 with greater than 94% recovery of the steviol glycoside.

Example 3

A series of solubility assays were carried out with steviol glycoside enhancer compositions and steviol glycoside. Steviol glycoside enhancer compositions comprising varying ratios of dicaffeoylquinic acid and dicaffeoylquinic salt to monocaffeoylquinic acid and monocaffeoylquinic salt were prepared and tested for their ability to solubilize steviol glycoside compositions. An accelerated solubility assay was performed with high concentrations of stevol glycoside (50,000 ppm, or 5% (wt)) and high concentrations of steviol glycoside solubility enhancer (35,714 ppm) to shorten the amount of time that the steviol glycoside would remain in solution to determine the effects of varying ratios of dicaffeoylquinic acid and dicaffeoylquinic salt to monocaffeoylquinic acid and monocaffeoylquinic salt on solubility of steviol glycoside compounds.

Chlorogenic acid, a monocaffeoylquinic acid, was obtained commercially (Penta Manufacturing Company, Livingston, New Jersey). A dicaffeoylquinic component was isolated from yerba mate. It contained 15% (wt) 3,4-dicaffeoylquinic acid, 45% (wt) 3,5-dicaffeoylquinic acid, 34% (wt) 4,5-dicaffeoylquinic acid, and <5% (wt) total monocaffeoylquinic acids. The steviol glycoside was 89% rebaudioside M and 8.2% rebaudioside D. A stock solution of monocaffeoylquinic acid was prepared and pH adjusted with concentrated sodium hydroxide such that a stock solution of monocaffeoylquinic acid of about 70% monocaffeoylquinic sodium salt resulted. A stock solution of dicaffeoylquinic acid was prepared and pH adjusted with concentrated sodium hydroxide such that a stock solution of dicaffeoylquinic acid of about 70% dicaffeoylquinic sodium salt resulted. The stock solutions, steviol glycoside, and distilled water were used to prepare three control compositions and seven test compositions in the concentrations and ratios as indicated below in Table Ex-1. The control and test compositions were prepared, aliquoted into glass vials, capped, and then heated at 80° C. for 5-10 minutes with periodic mixing. The vials were allowed to cool to room temperature (approximately 22° C.) and then stored at room temperature. The vials were visually inspected for crystal formation every day for the first two weeks and then weekly after that. The storage period that each composition remained in solution before crystals were seen is shown below in Table Ex-1.

The three control compositions comprised steviol glycoside without steviol glycoside solubility enhancer. One had 50,000 ppm (5% (wt/vol)) of the steviol glycoside, another had 30,000 ppm (3% (wt/vol)), and the third had 20,000 ppm (2% (wt/vol)). Each of the test compositions comprised steviol glycoside at 50,000 ppm (5% (wt/vol)) and steviol glycoside solubility enhancer at 35,714 ppm (3.57% (wt/vol)), which is a ratio of steviol glycoside to steviol glycoside solubility enhancer of about 1.4. Test compositions 1-7 comprised steviol glycoside solubility enhancers having weight ratios of the DCQ component to the MCQ component (i.e., the weight of the DCQ component divided by the weight of the MCQ component) of 10, 5, 3, 1, 0.33, 0.2, and 0.1, respectively.

TABLE Ex-1

Observations of control and test compositions over time

| Sample | Concentration monocaffeoylquinic acid (ppm) | Concentration dicaffeoylquinic acid (ppm) | Ratio of DCQ component to MCQ component | Storage period in solution |
|---|---|---|---|---|
| Control - 5% steviol glycoside | 0 | 0 | N/A | Did not go into solution |
| Control - 3% steviol glycoside | 0 | 0 | N/A | Did not go into solution |
| Control - 2% steviol glycoside | 0 | 0 | N/A | <1 hour |
| 1 | 3247 | 32467 | 10 | >33 days |
| 2 | 5952 | 29762 | 5 | >33 days |
| 3 | 8929 | 26786 | 3 | >33 days |
| 4 | 17857 | 17857 | 1 | 11 days |
| 5 | 26786 | 8929 | 0.33 | 7 days |
| 6 | 29762 | 5952 | 0.2 | 5 days |
| 7 | 32467 | 3247 | 0.1 | 4 days |

Table Ex-1 shows that each of the tests with the steviol glycoside solubility enhancers were able to effectively solubilize the steviol glycoside at 5% (wt/vol). The control composition with the same steviol glycoside concentration of 5% (wt/vol) was not dissolved even after several hours at 80° C. Even when the steviol glycoside concentration in the control was decreased to 2% (wt/vol), so it would go into solution at 80° C., the SG crashed out of solution in less than one hour, which is consistent with the equilibrium solubilities for rebaudioside M and rebaudioside D noted above. This alone demonstrates the remarkable effectiveness of the steviol glycoside solubility enhancers.

Surprisingly, the test compositions with ratios of the DCQ component to the MCQ component of greater than 1 had storage periods in solution, i.e., without visible precipitation, for over 10 days. That storage period was more than twice the storage period of the compositions with DCQ component: MCQ component ratios of 0.1 or 0.2 and over 50% longer than that for the sample with a ratio of 0.33. Therefore, steviol glycoside solubility enhancers with increasing ratios of the DCQ component to the MCQ component are more effective at solubilizing the steviol glycoside, with ratios of greater than 1 having greater effect.

The test composition with equal amounts of the DCQ component and the MCQ component were able to maintain a 5% (wt/vol) concentration of the steviol glycoside in solution for 11 days. That is a remarkable feat in its own right. All of the compositions with a ratio of the DCQ component to the MCQ component of three or greater maintained the steviol glycoside in solution for greater than four weeks at the time of drafting and may remain in solution much longer.

All publications, patents and patent applications are incorporated herein by reference. While in the foregoing specification, this invention has been described in relation to certain preferred aspects thereof, and many details have been set forth for purposes of illustration, it will be apparent to those skilled in the art that the invention is susceptible to additional aspects and that certain of the details herein may be varied considerably without departing from the basic principles of the invention.

The invention claimed is:

1. An aqueous steviol glycoside solution comprising:
one or more steviol glycosides; and
a steviol glycoside solubility enhancer comprising
a monocaffeoylquinic (MCQ) component that includes at least one compound selected from the group consisting of chlorogenic acid, neochlorogenic acid, cryptochlorogenic acid, and salts thereof; and
a dicaffeoylquinic (DCQ) component that includes at least one compound selected from the group consisting of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof;
wherein the MCQ component and the DCQ component together comprise more than 60% (wt) of the steviol glycoside solubility enhancer; and
wherein a weight ratio of the DCQ component to the MCQ component is at least 1;
wherein solubility of the one or more steviol glycosides in the aqueous steviol glycoside solution is higher than an equivalent solution lacking the steviol glycoside solubility enhancer; and
wherein when the aqueous steviol glycoside solution comprises at least 2% (wt) steviol glycoside and the one or more steviol glycosides remains in solution for at least 10 days when stored at 22° C.

2. The aqueous steviol glycoside solution of claim 1, wherein the MCQ component and the DCQ component together comprise more than 70% (wt) of the steviol glycoside solubility enhancer.

3. The aqueous steviol glycoside solution of claim 1, wherein the MCQ component and the DCQ component together comprise more than 80% (wt) of the steviol glycoside solubility enhancer.

4. The aqueous steviol glycoside solution of claim 1, wherein the MCQ component and the DCQ component together comprise more than 90% (wt) of the steviol glycoside solubility enhancer.

5. The aqueous steviol glycoside solution of claim 1, wherein the steviol glycoside solubility enhancer further comprising one or more compounds selected from the group consisting of caffeic acid, ferulic acid, p-coumaric acid, sinapic acid, quinic acid, 3-(3,4-dihydroxyphenyl) lactic acid, tartaric acid, chicoric acid, caftaric acid, monoferuloylquinic acids, diferuloylquinic acids, monocoumaroylquinic acids, dicoumaroylquinic acids, and salts thereof.

6. The aqueous steviol glycoside solution of claim 1, wherein the steviol glycoside solubility enhancer further comprising one or more compounds selected from the group consisting of caffeic acid, monoferuloylquinic acids, diferuloylquinic acids, and salts thereof.

7. The aqueous steviol glycoside solution of claim 1, wherein the weight ratio of the DCQ component to the MCQ component is between 1 and 20.

8. The aqueous steviol glycoside solution of claim 1, wherein solution comprises at least 2% (wt) steviol glycoside and the one or more steviol glycosides remains in solution for at least 10 days when stored at 22° C.

9. The aqueous steviol glycoside solution of claim 1, wherein solution comprises at least 3% (wt) steviol glycoside and the one or more steviol glycosides remains in solution for at least 10 days when stored at 22° C.

10. The aqueous steviol glycoside solution of claim 1, wherein solution comprises at least 5% (wt) steviol glycoside and the one or more steviol glycosides remains in solution for at least 10 days when stored at 22° C.

11. The aqueous steviol glycoside solution of claim 1, wherein the one or more steviol glycosides comprises rebaudioside M, rebaudioside D, or combinations thereof.

12. The aqueous steviol glycoside solution of claim 1, wherein the solution comprises at least 2% (wt) of a combination of rebaudioside M and rebaudioside D.

13. The aqueous steviol glycoside solution of claim 1, wherein the solution comprises at least 2% (wt) of a combination of rebaudioside M and rebaudioside D, and the combination of rebaudioside M and rebaudioside D are at least 75% (wt) of total steviol glycosides in the aqueous steviol glycoside solution.

14. The aqueous steviol glycoside solution of claim 1, wherein the solution comprises at least 2% (wt) of a combination of rebaudioside M and rebaudioside D, and the combination of rebaudioside M and rebaudioside D are at least 80% (wt) of total steviol glycosides in the aqueous steviol glycoside solution.

15. The aqueous steviol glycoside solution of claim 1, wherein the solution comprises at least 2% (wt) of a combination of rebaudioside M and rebaudioside D, and the combination of rebaudioside M and rebaudioside D are at least 90% (wt) of total steviol glycosides in the aqueous steviol glycoside solution.

16. The aqueous steviol glycoside solution of claim 1, wherein ratio of total steviol glycosides to steviol glycoside solubility enhancer is between 1:1 and 1:2.

17. The aqueous steviol glycoside solution of claim 1, wherein the solution comprises 1% (wt) to 10% (wt) steviol glycoside.

18. The aqueous steviol glycoside solution of claim 1, wherein the solution comprises 100 ppm to 900 ppm of the steviol glycoside solubility enhancer.

19. The aqueous steviol glycoside solution of claim 1, wherein steviol glycoside solubility enhancer comprises at least 50% (wt) of the DCQ component.

20. The aqueous steviol glycoside solution of claim 1, wherein steviol glycoside solubility enhancer comprises at least 60% (wt) of the DCQ component.

21. The aqueous steviol glycoside solution of claim 1, wherein steviol glycoside solubility enhancer comprises at least 70% (wt) of the DCQ component.

22. A non-alcoholic beverage comprising the aqueous steviol glycoside solution of claim 1 and having a pH of between 1.5 and 4.

23. An aqueous steviol glycoside solution comprising:
at least 2.0 wt % of total steviol glycosides comprising rebaudioside M and rebaudioside D; and
a steviol glycoside solubility enhancer comprising
a monocaffeoylquinic (MCQ) component that includes at least one compound selected from the group consisting of chlorogenic acid, neochlorogenic acid, cryptochlorogenic acid, and salts thereof; and
a dicaffeoylquinic (DCQ) component that includes at least one compound selected from the group consisting of 1,3-dicaffeoylquinic acid, 1,4-dicaffeoylquinic acid, 1,5-dicaffeoylquinic acid, 3,4-dicaffeoylquinic acid, 3,5-dicaffeoylquinic acid, 4,5-dicaffeoylquinic acid, and salts thereof;

wherein the MCQ component and the DCQ component together comprise more than 60% (wt) of the steviol glycoside solubility enhancer; and wherein a weight ratio of the DCQ component to the MCQ component is at least 1;

wherein solubility of the total steviol glycosides in the aqueous steviol glycoside solution is higher than an equivalent solution lacking the steviol glycoside solubility enhancer; and wherein the total steviol glycosides remain in solution for at least 10 days when stored at 22° C.

* * * * *